(12) United States Patent
Buevich et al.

(10) Patent No.: US 8,636,753 B2
(45) Date of Patent: *Jan. 28, 2014

(54) TEMPORARILY STIFFENED MESH PROSTHESES

(75) Inventors: Fatima Buevich, Highland Park, NJ (US); Frank Do, Jersey City, NJ (US); William McJames, Bellemeade, NJ (US); Satish Pulapura, Bridgewater, NJ (US); William Edelman, Sharon, MA (US); Arikha Moses, NY, NY (US); Mason Diamond, Wayne, NJ (US); Shari Timothy, Brunswick, NJ (US)

(73) Assignee: TYRX, Inc., Monmouth Junction, NJ (US)

( * ) Notice: Subject to any disclaimer, the term of this patent is extended or adjusted under 35 U.S.C. 154(b) by 340 days.

This patent is subject to a terminal disclaimer.

(21) Appl. No.: 11/672,929

(22) Filed: Feb. 8, 2007

(65) Prior Publication Data

US 2007/0198040 A1 Aug. 23, 2007

Related U.S. Application Data

(60) Provisional application No. 60/864,597, filed on Nov. 6, 2006, provisional application No. 60/771,827, filed on Feb. 8, 2006.

(51) Int. Cl.
*A61F 2/02* (2006.01)
*B05D 1/02* (2006.01)

(52) U.S. Cl.
USPC ........ 606/151; 424/426; 427/2.31; 623/23.75

(58) Field of Classification Search
None
See application file for complete search history.

(56) References Cited

U.S. PATENT DOCUMENTS

| | | | |
|---|---|---|---|
| 4,298,997 A | 11/1981 | Rybka | |
| 4,326,532 A | 4/1982 | Hammar | |
| 4,642,104 A | 2/1987 | Sakamoto et al. | |
| 4,713,073 A | 12/1987 | Reinmuller | |
| 4,769,038 A | 9/1988 | Bendavid | |
| 4,846,844 A | 7/1989 | De Leon et al. | |
| 4,980,449 A | 12/1990 | Kohn et al. | |
| 5,099,060 A | 3/1992 | Kohn et al. | |
| 5,216,115 A | 6/1993 | Kohn et al. | |
| 5,217,493 A * | 6/1993 | Raad et al. | 623/11.11 |
| 5,279,594 A | 1/1994 | Jackson | |
| 5,295,978 A | 3/1994 | Fan | |
| 5,317,077 A | 5/1994 | Kohn et al. | |
| 5,362,754 A | 11/1994 | Raad | |
| 5,417,671 A | 5/1995 | Jackson | |
| 5,512,055 A | 4/1996 | Domb | |
| 5,554,147 A | 9/1996 | Batich | |
| 5,587,507 A | 12/1996 | Kohn et al. | |
| 5,607,417 A | 3/1997 | Batich | |
| 5,607,477 A | 3/1997 | Schindler et al. | |
| 5,614,284 A * | 3/1997 | Kranzler et al. | 428/138 |
| 5,624,704 A | 4/1997 | Darouiche | |
| 5,658,995 A | 8/1997 | Kohn et al. | |
| 5,670,602 A | 9/1997 | Kohn et al. | |
| 5,676,146 A * | 10/1997 | Scarborough | 600/431 |
| 5,722,992 A | 3/1998 | Goldmann | |
| 5,755,758 A | 5/1998 | Woloszko | |
| 5,756,145 A | 5/1998 | Darouiche | |
| 5,810,786 A | 9/1998 | Jackson | |
| 5,834,051 A | 11/1998 | Woloszko | |
| 5,853,745 A | 12/1998 | Darouiche | |
| 5,902,283 A | 5/1999 | Darouiche | |
| 6,013,853 A | 1/2000 | Athanasiou | |
| 6,048,521 A | 4/2000 | Kohn et al. | |
| 6,096,070 A | 8/2000 | Ragheb | |
| 6,099,562 A | 8/2000 | Ding | |
| 6,103,255 A | 8/2000 | Levene et al. | |
| 6,120,491 A * | 9/2000 | Kohn et al. | 604/502 |
| 6,162,487 A | 12/2000 | Darouiche | |
| RE37,160 E | 5/2001 | Kohn et al. | |
| 6,267,772 B1 | 7/2001 | Mulhauser et al. | |

(Continued)

FOREIGN PATENT DOCUMENTS

EP 0971753 1/2000
JP 07-000430 A 1/1995

(Continued)

OTHER PUBLICATIONS

Reit, Annals of Surgery, 237, 2003.*

(Continued)

*Primary Examiner* — Robert A Wax
*Assistant Examiner* — William Craigo
(74) *Attorney, Agent, or Firm* — Lerner, David, Littenberg, Krumholz & Mentlik, LLP

(57) ABSTRACT

The present invention relates to medical prostheses and methods of manufacturing those devices. In particular, the prostheses are temporarily stiffened meshes with particular coatings to provide initial stiffness and thereby permit easier surgical handling for treatment or reconstruction of soft tissue defects. Preferred embodiments include surgical meshes coated with one or more biodegradable polymers that can act as a stiffening agent by coating the filaments or fibers of the mesh to temporarily immobilize the contact points of those filaments or fibers and/or by increasing the stiffness of the mesh by at least 1.1 times its original stiffness. The devices of the invention can also provide relief from various post-operative complications associated with their implantation, insertion or surgical use. By including biologically active agents and/or drugs in the coating, the devices provide prophylaxis for and can alleviate side effects or complications associated with the surgery or use of prostheses in general.

25 Claims, 6 Drawing Sheets

(56) References Cited

U.S. PATENT DOCUMENTS

| | | | |
|---|---|---|---|
| 6,306,176 B1 | 10/2001 | Whitbourne | |
| 6,319,264 B1 | 11/2001 | Tormala | |
| 6,319,492 B1 | 11/2001 | Kohn et al. | |
| 6,335,029 B1 | 1/2002 | Kamath | |
| 6,337,198 B1 | 1/2002 | Levene et al. | |
| RE37,795 E | 7/2002 | Kohn et al. | |
| 6,461,644 B1 | 10/2002 | Jackson | |
| 6,475,434 B1 | 11/2002 | Darouiche | |
| 6,475,477 B1 | 11/2002 | Kohn et al. | |
| 6,514,286 B1 | 2/2003 | Leatherbury | |
| 6,548,569 B1 | 4/2003 | Williams et al. | |
| 6,558,686 B1 | 5/2003 | Darouiche | |
| 6,584,363 B2 | 6/2003 | Heil | |
| 6,589,546 B2 | 7/2003 | Kamath | |
| 6,589,591 B1 | 7/2003 | Mansouri | |
| 6,602,497 B1 | 8/2003 | Kohn et al. | |
| 6,656,488 B2 | 12/2003 | Yi et al. | |
| 6,719,987 B2 | 4/2004 | Burrell et al. | |
| 6,719,991 B2 | 4/2004 | Darouiche et al. | |
| 6,753,071 B1 | 6/2004 | Pacetti | |
| 6,838,493 B2 * | 1/2005 | Williams et al. | 523/124 |
| 6,852,308 B2 | 2/2005 | Kohn et al. | |
| 6,887,270 B2 | 5/2005 | Miller et al. | |
| 6,916,483 B2 | 7/2005 | Ralph | |
| 6,916,868 B2 | 7/2005 | Kemnitzer | |
| 6,961,610 B2 | 11/2005 | Yang | |
| 6,968,234 B2 | 11/2005 | Stokes | |
| 6,981,944 B2 * | 1/2006 | Jamiolkowski et al. | 600/30 |
| 6,986,899 B2 | 1/2006 | Hossainy | |
| 6,991,802 B1 | 1/2006 | Ahola | |
| 7,005,454 B2 | 2/2006 | Brocchini | |
| 7,056,493 B2 | 6/2006 | Kohn et al. | |
| 7,195,615 B2 | 3/2007 | Tan | |
| 7,250,154 B2 | 7/2007 | Kohn et al. | |
| 7,271,234 B2 | 9/2007 | Kohn et al. | |
| 7,326,425 B2 | 2/2008 | Kohn et al. | |
| 2002/0072694 A1 * | 6/2002 | Snitkin et al. | 602/4 |
| 2002/0151668 A1 | 10/2002 | James et al. | |
| 2003/0091609 A1 * | 5/2003 | Hendriks | 424/423 |
| 2003/0138488 A1 | 7/2003 | Kohn et al. | |
| 2003/0153983 A1 | 8/2003 | Miller et al. | |
| 2003/0175410 A1 | 9/2003 | Campbell et al. | |
| 2003/0216307 A1 | 11/2003 | Kohn et al. | |
| 2003/0224033 A1 | 12/2003 | Li | |
| 2004/0010276 A1 * | 1/2004 | Jacobs et al. | 606/153 |
| 2004/0043052 A1 | 3/2004 | Hunter et al. | |
| 2004/0146546 A1 | 7/2004 | Gravett | |
| 2004/0147688 A1 | 7/2004 | Kemnitzer et al. | |
| 2004/0172048 A1 * | 9/2004 | Browning | 606/151 |
| 2004/0186528 A1 | 9/2004 | Ries | |
| 2004/0186529 A1 | 9/2004 | Bardy et al. | |
| 2004/0209538 A1 | 10/2004 | Klinge et al. | |
| 2004/0220249 A1 | 11/2004 | Puder et al. | |
| 2004/0220665 A1 | 11/2004 | Hossainy | |
| 2004/0245671 A1 | 12/2004 | Smit | |
| 2004/0253293 A1 | 12/2004 | Shafiee | |
| 2004/0254334 A1 | 12/2004 | James et al. | |
| 2005/0008671 A1 | 1/2005 | Van Antwerp | |
| 2005/0015102 A1 | 1/2005 | Chefitz | |
| 2005/0031669 A1 | 2/2005 | Shafiee | |
| 2005/0052466 A1 | 3/2005 | Frazer et al. | |
| 2005/0101692 A1 | 5/2005 | Sohier et al. | |
| 2005/0112171 A1 | 5/2005 | Tang | |
| 2005/0113849 A1 | 5/2005 | Popadiuk | |
| 2005/0118227 A1 | 6/2005 | Kohn et al. | |
| 2005/0143817 A1 | 6/2005 | Hunter et al. | |
| 2005/0147690 A1 | 7/2005 | Masters et al. | |
| 2005/0148512 A1 | 7/2005 | Hunter et al. | |
| 2005/0149157 A1 * | 7/2005 | Hunter et al. | 607/119 |
| 2005/0161859 A1 | 7/2005 | Miller et al. | |
| 2005/0163821 A1 | 7/2005 | Sung et al. | |
| 2005/0165203 A1 | 7/2005 | Kohn et al. | |
| 2005/0169959 A1 | 8/2005 | Hunter | |
| 2005/0177225 A1 | 8/2005 | Hunter et al. | |
| 2005/0181977 A1 | 8/2005 | Hunter et al. | |
| 2005/0208095 A1 | 9/2005 | Hunter et al. | |
| 2005/0208664 A1 | 9/2005 | Keegan et al. | |
| 2005/0209664 A1 | 9/2005 | Hunter et al. | |
| 2005/0228471 A1 | 10/2005 | Williams et al. | |
| 2005/0233062 A1 | 10/2005 | Hossainy | |
| 2005/0245637 A1 | 11/2005 | Hossainy | |
| 2005/0267543 A1 | 12/2005 | Heruth | |
| 2006/0009806 A1 | 1/2006 | Heruth | |
| 2006/0025852 A1 | 2/2006 | Armstrong et al. | |
| 2006/0034769 A1 | 2/2006 | Kohn et al. | |
| 2006/0035854 A1 | 2/2006 | Goldstein et al. | |
| 2006/0052466 A1 | 3/2006 | Handa | |
| 2006/0062825 A1 | 3/2006 | Maccecchini | |
| 2006/0067908 A1 | 3/2006 | Ding | |
| 2006/0073182 A1 | 4/2006 | Wong | |
| 2006/0095134 A1 | 5/2006 | Trieu | |
| 2006/0115449 A1 | 6/2006 | Pacetti | |
| 2006/0121179 A1 | 6/2006 | Pacetti | |
| 2006/0134168 A1 | 6/2006 | Chappa | |
| 2006/0142786 A1 | 6/2006 | Mathisen | |
| 2006/0147492 A1 | 7/2006 | Hunter et al. | |
| 2006/0204440 A1 | 9/2006 | Kohn et al. | |
| 2006/0246103 A1 | 11/2006 | Ralph et al. | |
| 2007/0196421 A1 | 8/2007 | Hunter et al. | |
| 2007/0198040 A1 | 8/2007 | Buevich et al. | |
| 2007/0213416 A1 | 9/2007 | Handa et al. | |
| 2007/0286928 A1 | 12/2007 | Sarmas et al. | |
| 2007/0299155 A1 | 12/2007 | Carpenter et al. | |
| 2008/0107709 A1 | 5/2008 | Kohn et al. | |
| 2008/0128315 A1 | 6/2008 | Buevich et al. | |
| 2008/0132922 A1 | 6/2008 | Buevich et al. | |
| 2008/0241212 A1 | 10/2008 | Moses et al. | |
| 2009/0018559 A1 | 1/2009 | Buevich et al. | |
| 2009/0029961 A1 | 1/2009 | Modak et al. | |
| 2009/0088548 A1 | 4/2009 | Moses et al. | |
| 2010/0015237 A1 | 1/2010 | Moses et al. | |
| 2010/0074940 A1 | 3/2010 | Schwartz et al. | |
| 2010/0129417 A1 | 5/2010 | Moses et al. | |
| 2010/0130478 A1 | 5/2010 | Moses et al. | |
| 2010/0167992 A1 | 7/2010 | Schwartz et al. | |
| 2010/0168808 A1 | 7/2010 | Citron | |

FOREIGN PATENT DOCUMENTS

| | | |
|---|---|---|
| JP | 2000-512519 A | 9/2000 |
| JP | 2002-500065 A | 1/2002 |
| JP | 2002-522112 A | 7/2002 |
| JP | 2004-524059 A | 8/2004 |
| JP | 2004-535866 A | 12/2004 |
| JP | 2005-152651 A | 6/2005 |
| JP | 2007500552 A | 1/2007 |
| WO | WO 95/08305 | 3/1995 |
| WO | 9747254 A1 | 12/1997 |
| WO | WO 9832474 | 7/1998 |
| WO | WO 99/24107 | 5/1999 |
| WO | 9934750 A1 | 7/1999 |
| WO | WO 99/52962 | 10/1999 |
| WO | WO 01/49249 | 7/2001 |
| WO | WO 01/49311 | 7/2001 |
| WO | WO 03/091337 | 11/2003 |
| WO | 2004071485 A1 | 8/2004 |
| WO | WO 2004071485 A1 * | 8/2004 |
| WO | 2005/011767 A1 | 2/2005 |
| WO | WO 2005055972 | 6/2005 |
| WO | 2006133569 A1 | 12/2006 |
| WO | 2007056134 A2 | 5/2007 |
| WO | WO 2007056134 | 5/2007 |
| WO | WO 2008/127411 | 10/2008 |
| WO | WO 2008/136856 | 11/2008 |
| WO | WO 2008/121816 | 12/2008 |
| WO | WO 2009/113972 | 9/2009 |

OTHER PUBLICATIONS

Darouiche, NEJM, 340, 1999.*
Greca, Hernia, 5, 2001.*
Furacin, 2013 (obtained from http://www.drugs.com/cons/furacin-topical.html).*
Zoll, Annals of Surgery, Sep. 1964.*

(56) References Cited

OTHER PUBLICATIONS

International Search Report from PCT/US07/83841, mailed Oct. 31, 2008, 3 pp.
Written Opinion from PCT/US07/83841, mailed Oct. 31, 2008, 5 pp.
Cabell et al., 2004, "Increasing rates of cardiac device infections among Medicare beneficiaries: 1990-1999," American Heart Journal 147(4):582-586.
Costerton et al., 2003, "The application of biofilm science to the study and control of chronic bacterial infections," Journal of Clinical Investigation 112(10):1466-1477.
Falagas et al., 2007, :Rifampicin-impregnated central venous catheters: a meta-analysis of randomized controlled trials, J. Antimicrobial Chemotherapy 59:359-369.
Lau et al., 2003, "Randomized clinical trial of postoperative subfascial infusionwith bupivacaine following ambulatory open mesh repair of inguinal hernia." Dig.Surg. 20(4):285-289.
Sohail et al., 2007, "Management and Outcome of Permanent Pacemaker and Implantable Cardioverter-Defibrillator Infections," Journal of the American College of Cardiology 49(18):1851-1859.
Wilkoff et al., 2007, "How to treat and identify device infections," Heart Rhythm 4(11):1467-1470.
Yourassowsky, E. et al., "Combination of Minocycline and Rifampicin against Methicillin- and Gentamicin-Resistant *Staphylococcus aureus*," J. Clin. Pathol., 1981, pp. 559-563, vol. 34.
Clumeck, N. et al., "Treatment of Severe *Staphylococcal* Infections with a Rifampicin-Minocycline Association," J. Antimicrob. Chemother., 1984, pp. 17-22, vol. 13(SuppC).
Zinner, S. H. et al., "Antistaphylococcal Activity of Rifampin with Other Antibiotics," J. Infect. Dis., Oct. 1981, pp. 365-371, vol. 144(4).
Kohn, J., "Implants: The Biodegradable Future," Mar. 1, 2006, <URL: http://www.medicaldevice-network.com/features/feature 168/>.
van't Riet, M. et al., "Prevention of Adhesion Formation to Polypropylene Mesh by Collagen Coating," Surg. Endosc., 2004, pp. 681-685, vol. 18.
Office Action for U.S. Appl. No. 12/058,060, mailed Jan. 22, 2010, 10 pages.
Office Action for U.S. Appl. No. 11/936,049, mailed Apr. 14, 2010, 18 pages.
International Search Report and Written Opinion for International Application No. PCT/US2008/058652, mailed Sep. 12, 2008, 7 pages.
International Preliminary Report on Patentability for International Application No. PCT/US2008/058652, issued Sep. 29, 2009, 5 pages.
International Search Report and Written Opinion for International Application No. PCT/US2007/083843, mailed Sep. 11, 2008, 7 pages.
International Preliminary Report on Patentability for International Application No. PCT/US2007/083843, issued May 12, 2009, 7 pages.
International Preliminary Report on Patentability for International Application No. PCT/US2007/083841, issued May 12, 2009, 6 pages.
Ajmal, N. et al., "The Effectiveness of Sodium 2-Mercaptoethane Sulfonate (Mesna) in Reducing Capsular Formation around Implants in a Rabbit Model," 2003, Plastic and Reconstructive Surgery, vol. 112(5), pp. 1455-1461.
Agostinho, A. et al., "Inhibition of *Staphylococcus aureus* Biofilms by a Novel Antibacterial Envelope for Use with Implantable Cardiac Devices," 2009, vol. 2(3), pp. 193-198.
Bach, A. et al., "Retention of antibacterial activity and bacterial colonization of antiseptic-bonded central venous catheters," J. Antimicrob. Chemother., 1996, vol. 37(2), pp. 315-322.
Baddour, L. M. et al., "Nonvalvular cardiovascular device-related infections," Circulation, 2003, vol. 108, pp. 2015-2031.
Chamis, A. L. et al., "*Staphylococcus aureus* bacteremia in patients with permanent pacemakers or implantable cardioverter-defibrillators," Circulation, 2001, vol. 104, pp. 1029-1033.
Collin, G. R., "Decreasing catheter colonization through the use of an antiseptic-impregnated catheter: a continuous quality improvement project," Chest., 1999, vol. 115(6), pp. 1632-1640.
Da Costa, A. et al., "Antibiotic prophylaxis for permanent pacemaker implantation: A meta-analysis," Circulation, 1998, vol. 97, pp. 1796-1801.
Darouiche, R. O. et al., "A comparison of two antimicrobial-impregnated central venous cathethers," The New England Journal of Medicine, 1999, vol. 340(1), pp. 1-8.
Darouiche, R. O., "Antimicrobial approaches for preventing infections associated with surgical implants," Clin. Infect. ,Dis., 2003, vol. 36, pp. 1284-1289.
Darouiche, R. O., "Treatment of infections associated with surgical implants," New England Journal of Medicine, 2004, vol. 350, pp. 1422-1429.
Darouiche, R. O. et al., "Efficacy of antimicrobial-impregnated silicone sections from penile implants in preventing device colonization in an animal model," Urology, 2002, vol. 59, pp. 303-307.
Darouiche, R. O. et al., "In vivo efficacy of antimicrobe-impregnated saline-filled silicone implants," Plast. Reconstr. Surg., 2002, vol. 109(4), pp. 1352-1357.
Donlan, R. M., "Biofilms and device-associated infections," Emerging Infectious Diseases, 2001, vol. 7(2), pp. 277-281.
Engelmayr, G. C., Jr. et al., "A novel bioreactor for the dynamic flexural stimulation of tissue engineered heart valve biomaterials," Biomaterials, 2003, vol. 24, pp. 2523-2532.
George, S. J. et al., "Antiseptic-impregnated central venous catheters reduce the incidence of bacterial colonization and associated infection in immunocompromised transplant patients," Eur. J. Anaesthesiol., 1997, vol. 14, pp. 428-431.
Greca, F. H. et al., "The influence of differing pore sizes on the biocompatibility of two polypropylene meshes in the repair of abdominal defects," Hernia, 2001, vol. 5, pp. 59-64.
Hambraeus, A. et al., "Bacterial contamination in a modem operating suite, 2. Effect of a zoning system on contamination of floors and other surfaces," J. Hyg., 1978, vol. 80, pp. 57-67.
Hayes, B. B. et al., "Evaluation of percutaneous penetration of natural rubber latex proteins," Toxicol. Sci., 2000, vol. 56, pp. 262-270.
Hospital Infections Program, National Centre for Infectious Disease, CDC, "Public Health Focus: Surveillance, Prevention, and Control of Nosocomial Infections," MMWR Weekly, 1992, vol. 41, pp. 783-787.
Khodorova, A. B. et al., "The addition of dilute epinephrine produces equieffectiveness of bupivacaine enantiomers for cutaneous analgesia in the rat," Anesth. Analg., 2000, vol. 91, pp. 410-416.
Kramer, C. et al., "A fatal overdose of transdermally administered fentanyl," J. Am. Osteopath. Assoc., 1998, vol. 98(7), pp. 385-386.
Leblanc, K. A., et al., "Evaluation of continuous infusion of 0.5% bupivacaine by elastomeric pump for postoperative pain management following open inguinal hernia repair," J. Am. Coll. Surg., 2005, vol. 200(2), pp. 198-202.
Li, H. et al., "Antibacterial activity of antibiotic coated silicon grafts," J. Urol., 1998, vol. 160(5), pp. 1910-1913.
Maki, D. G. et al., "Engineering out the risk of infection with urinary catheters," Emerging Infectious Diseases, 2001, vol. 7(2), pp. 342-347.
Maki, D. G. et al., "Prevention of central venous catheter-related blood stream infection by use of an antiseptic-impregnated catheter: A randomized, controlled trial," Ann. Intern. Med., 1997, vol. 127, pp. 257-266.
Meakins, J. L., "Prevention of postoperative infection," in ACS Surgery: Principals and Practice, American College of Surgeons, 2005, pp. 1-20.
Morrow, T. J. et al, "Suppression of bulboreticular unit responses to noxious stimuli by analgesic mesencephalic stimulation," Somatosens. Res., 1983, vol. 1, pp. 151-168.
Pearson, M. L., et al., "Reducing the risk for catheter-related infections: A new strategy," Ann. Intern. Med., 1997, vol. 127(4), pp. 304-306.
Perencevich, E. N. et.al., "Health and economic impact of surgical site infections diagnosed after hospital discharge," Emerging Infect. Dis., 2003, vol. 9(2), pp. 196-203.

(56) References Cited

OTHER PUBLICATIONS

Raad, I. et al., "Central venous catheters coated with minocycline and rifampin for the prevention of catheter-related colonization and bloodstream infections: A randomized, double-blind trial," Ann. Intern. Med., 1997, vol. 127(4), pp. 267-274.
Sanchez, B. et al., "Local anesthetic infusion pumps improve post-operative pain after inguinal hernia repair,"The American Surgeon, 2004, vol. 70, pp. 1002-1006.
Segura, M. et al., "A clinical trial on the prevention of catheter-related sepsis using a new hub model," Ann. Surg., 1996, vol. 223(4), pp. 363-369.
Tennenberg, S. et al., "A prospective randomized trial of an antibiotic- and antiseptic-coated central venous catheter in the prevention of catheter-related infections," Arch. Surg., 1997, vol. 132, pp. 1348-1351.
Final Office Action for U.S. Appl. No. 11/936,049, mailed Dec. 21, 2010, 20 pages.
Final Office Action for U.S. Appl. No. 12/058,060, mailed Oct. 13, 2010, 19 pages.
Areolar Tissue, The Free Dictionary, May 2011.
Rupp, Clinical Infectious Diseases, vol. 19, 1994.
Green, Clinical Cornerstone, vol. 3, 2001.
Australian Examination Report for Application No. 2007344645 dated Mar. 8, 2012.
Extended European Search Report for Application No. 07873600 dated Aug. 30, 2012.
Extended European Search Report for Application No. EP07874257 dated Aug. 29, 2012.
Japanese Office Action for Application No. 2009-535508 dated Aug. 14, 2012.
Prevent, WordNet, 2011.
TyRx Pharama, Inc., TyRx Press Releases, TyRx Announces FDA 510(k) Filing for New Antibiotic Eluting Surgical Mesh, USA, Jan. 17, 2006, [searched on May 2, 2012] URL, http://www.tyrx.com/Collateral/Documents/TyRx%20English-US/01-17-06-pr.pdf.
TyRx Pharama, Inc., TyRx Press Releases, TyRx Announces FDA 510(k) Filing for New Surgical Mesh, USA, May 17, 2005, [searched on May 2, 2012], URL, http://www.tyrx.com/Collateral/Documents/TyRx%20English-US/10-17-05-pr.pdf.
TyRx Pharama, Inc., TyRx Press Releases, TyRx Pharama's Anesthetic Coated Surgical Mesh Combination Product Assigned to "Device" Center at FDA, USA, Jan. 9, 2006, [searched on May 2, 2012], URL, http://www.tyrx.com/Collateral/Documents/TyRx%20English-US/01-09-06-pr.pdf.
TyRx Pharma, Inc. Announces Submission of a Premarket Application for PIVIT CRM, TYRX Press Releases [searched on Apr. 16, 2012], USA, Oct. 16, 2006, URL, http://www.tyrx.com/Collateral/Documents/TyRx%20English-US/10-16-06-pr.pdf.
New product introduction at Tyrx Pharma, Inc. The Journal of Product and Brand management, US, Dec. 1, 2006, p. 468-472 The publication date has been recognized based on the description in http://www.ingentaconnect.com/content/mcb/096/2006/00000015/00000007/art00008, "Publication date: Dec. 1, 2006"[Date of Search Apr. 16, 2012].
Japanese Office Action for Application No. 2009-535509 dated Apr. 15, 2013.
Parsonnet, Pacing and Clinical Electrophysiology, 17, 1994.
Enhancing Medical Devices, Sep. 2005, <URL: http://www.tyrx.com/Collateral/documents/TyRx%20English-US/03-06-pr.p.df>.
Japanese Office Action for Application No. 2010-502992 dated Apr. 17, 2013.
Canadian Office Action for Application No. CA/2667873 dated Feb. 11, 2013.
Canadian Office Action for Application No. 2,667,867 dated Aug. 19, 2013.

* cited by examiner

Total ZOI (diameter, mm)

↓

TEMPORARILY STIFFENED MESH PROSTHESES

This application claims priority under 35 U.S.C. §119(e) of U.S. Provisional Patent Application No. 60/864,597, filed Nov. 6, 2006 and of U.S. Provisional Patent Application No. 60/771,827, filed Feb. 8, 2006 and incorporated herein by reference.

FIELD OF THE INVENTION

The present invention relates to medical prostheses and methods of manufacturing those devices. In particular, the prostheses are temporarily stiffened meshes with particular coatings to provide initial stiffness and thereby permit easier surgical handling for treatment or reconstruction of soft tissue defects. Preferred embodiments include surgical meshes coated with one or more biodegradable polymers that can act as a stiffening agent by coating the filaments or fibers of the mesh to temporarily immobilize the contact points of those filaments or fibers and/or by increasing the stiffness of the mesh by at least 1.1 times its original stiffness. The devices of the invention can also provide relief from various post-operative complications associated with their implantation, insertion or surgical use. By including biologically active agents and/or drugs in the coating, the devices provide prophylaxis for and can alleviate side effects or complications associated with the surgery or use of prostheses in general.

BACKGROUND OF THE INVENTION

Prosthetic implants such as meshes, combination mesh products or other porous prostheses are commonly used to provide a physical barrier between types of tissue or extra strength to a physical defect in soft tissue. However, such devices are often associated with post-surgical complications including post-implant infection, pain, excessive scar tissue formation and shrinkage of the prosthesis or mesh. Excessive scar tissue formation, limited patient mobility, and chronic pain are often attributed to the size, shape, and mass of the implant and a variety of efforts have been undertaken to reduce the amount of scar tissue formation. For example, lighter meshes using smaller fibers, larger weaves, and/or larger pore sizes as well as meshes woven from both non-resorbable and resorbable materials are in use to address these concerns.

For treating acute pain and infection, patients with implanted prostheses are typically treated post-operatively with systemic antibiotics and pain medications. Patients will occasionally be given systemic antibiotics prophylactically; however, literature review of clinical trials does not indicate that systemic antibiotics are effective at preventing implant-related infections.

Many types of soft tissue defects are known. For example, hernias occur when muscles and ligaments tear and allow the protrusion of fat or other tissues through the abdominal wall. Hernias usually occur because of a natural weakness in the abdominal wall or from excessive strain on the abdominal wall, such as the strain from heavy lifting, substantial weight gain, persistent coughing, or difficulty with bowel movements or urination. Eighty percent of all hernias are located near the groin but can also occur below the groin (femoral), through the navel (umbilical), and along a previous incision (incisional or ventral). Almost all hernia repair surgeries are completed with the insertion of a barrier or prosthesis to prevent their reoccurrence. Therefore products used in the management of hernias require some measure of permanent strength. The most commonly employed woven meshes are crafted from polypropylene fibers using various weaves. Tightly woven meshes with the highest strength characteristics and stiffness are very easy for the surgeon to implant; however, there appears to be a positive correlation between the tightness of the weave (correlated to surface area and stiffness), lack of patient mobility, and chronic pain. Newer meshes have larger pore structures and while they are more flexible, they are also more difficult to implant by surgeons. They are extremely difficult for laparoscopic repair, as they have very little recoil associated with them and, when rolled up to insert, they cannot be reflattened and positioned in a quick and efficient manner by the surgeon. Hence, a need still exists for surgical meshes, including hernia meshes, that have sufficient stiffness to facilitate handling and ease of insertion during surgery, yet are or can become sufficiently flexible to be comfortable after implantation.

Surgical meshes that have been manipulated to improve handling, insertiona and positioning post-insertion are known in the art, but do not employ larger-pore mesh construction. For example, a laparoscopic surgical mesh with extruded monofilament PET coils or rings (e.g., the Bard® Composix® Kugel® hernia patch) increases the overall stiffness of the device and gives a shape memory to the device but does not readily allow for drug loading of the mesh, can not provide temporary stiffening of the mesh component, and can not be further shaped into a fixed three-dimensional structure after manufacture without further processing or alteration. Similarly, meshes with reinforced edges have been produced (e.g., Bard® Visilex®). These meshes have the same disadvantages as those with coils or rings. Additionally, the Kugel patch ring has been reported to break under conditions of use, causing patient morbidity and mortality.

Meshes produced from a co-weave of a biodegradable material with a non-biodegradable material have been described, e.g., the Johnson & Johnson Vypro® and Vypro II® meshes. In these meshes, polypropylene and polyglactin filaments are braided together before being knitted into a mesh. Such meshes do not change stiffness upon implant as the polyglactin fibers are very fine and flexible. The biodegradable fibers in the VyPro meshes in concert with its particular fiber weave imparts additional flexibility to the mesh such that it distends more easily than the surrounding tissue so that it is more flexible than an equivalent polypropylene fiber mesh with the same weave. Moreover, because the biodegradable polymers of that mesh may be subjected to high temperatures to produce fibers and filaments suitable for weaving, it drastically limits the drugs or biologically active agents that can be included in a biodegradable layer since, under such conditions, the vast majority of biologically-active agents and drugs are unable to withstand the manufacturing temperatures involved in fiber and filament formation. If three-dimensional structures are desired for such meshes, they must undergo further processing to attain such shapes. Finally, these meshes are often more difficult for surgeons to anchor in place because the polyglactin fiber cannot withstand the suturing tension.

The present invention overcomes these disadvantages by providing temporarily stiffened and shapeable meshes.

SUMMARY OF THE INVENTION

The present invention is directed to a medical prosthesis comprising a mesh and one or more coating which temporarily stiffens the mesh to at least 1.1 times its original stiffness. The coatings on such meshes do not alter the integrity of the mesh and thus allow the mesh to remain porous. In general, the coatings do not substantially alter the porosity of the mesh. More particularly, the medical prostheses of the invention comprise a mesh with one or more coatings with at least one of the coatings comprising a stiffening agent that coats the filaments or fibers of the mesh so to temporarily immobilize the contact points of those filaments or fibers. Again, the coatings on such meshes do not alter the integrity strength of the underlying mesh and thus allow the mesh to remain porous after coating. The meshes are capable of substantially reverting to their original stiffness under conditions of use.

The stiffening agents of the invention can selectively, partially or fully coat the contact points of the filaments or said fibers of the mesh to create a coating. The contact points generally include the knots of woven meshes. Such coating are preferably positioned on the mesh in a templated pattern or in an array such as might be deposited with ink-jet type technology, including computer controlled deposition techniques. Additionally, the coatings can be applied on one or both sides of the mesh.

In accordance with the invention, the medical prostheses of the invention include meshes that have been formed into three-dimensional shapes with the shape being maintained by the strength imparted by the coating. Such meshes flat or substantially flat before coating and the application of the coating provides the structural support for the three-dimensional shape. any shape can be formed, including curved meshes and conical shapes.

The stiffening agents include but are not limited to hydrogels and/or biodegradable polymers. One or more biodegradable polymers can be used per individual coating layer. Preferred biodegradable polymer comprises one or more tyrosine-derived diphenol monomer units as polyarylates, polycarbonates or polyiminocarbonates.

In another aspect of the invention, the medical prosthesis of the invention have at least one of the coatings that further comprises one or more drugs. Such drugs include, but are not limited to, antimicrobial agents, anesthetics, analgesics, anti-inflammatory agents, anti-scarring agents, anti-fibrotic agents and leukotriene inhibitors.

Yet another aspect of the invention is directed to a process for coating a mesh with a stiffening agent that coats the filaments or fibers of the mesh to temporarily immobilize the contact points of the filaments or fibers of said mesh by (a) preparing a coating solution comprising a solvent and the stiffening agent; (b) spraying a mesh one or more times to provide a sufficient amount of solution on the said mesh to produce a coating having a thickness and placement sufficient to temporarily immobilize the contact points of the filaments or fibers of said mesh that coats filaments or fibers; and (c) drying the mesh to produce the desired coating.

Still another aspect of the invention provides a method for producing a shaped or three-dimensional medical prosthesis by (a) forming a mesh into a desired shape or three-dimensional shape; (b) applying a stiffening agent to the mesh to coat the filaments or fibers of the mesh; (c) allowing the agent to dry, set or cure causing the mesh to temporarily immobilize contact points of the filaments or fibers of said mesh and thereby to retain the desired shape. Shapes can be formed by affixing the mesh to a mold or framework to created the desired shape, applying the agent to the mesh while so affixed, and removing the mesh from the mold or framework after the agent has dried, set or cured sufficiently to allow the mesh to retain its shape.

The coated meshes of the invention are capable of releasing one or more drugs into surrounding bodily tissue such that the drug reduces or prevents an implant- or surgery-related complication. For example, the surgical mesh coatings can include an anesthetic agent such that agent seeps into the surrounding bodily tissue, bodily fluid, or systemic fluid in a predictable manner and at rate sufficient to attenuate the pain experienced at the site of implantation. In another example, the surgical meshes coatings can include an anti-inflammatory agent such that the anti-inflammatory agent seeps into the surrounding bodily tissue, bodily fluid or systemic fluid in a predictable manner and at a rate sufficient to reduce the swelling and inflammation associated implantation of the mesh. Still a further example, the surgical mesh coatings can include an antimicrobial agent such that the antimicrobial agent is released into the surrounding bodily tissue, bodily fluid, or systemic fluid in a predictable manner and at a therapeutically-effective dose to provide a rate of drug release sufficient to prevent colonization of the mesh (and/or surgical implantation site) by bacteria for a minimum of the period of time following surgery necessary for initial healing of the surgical incision.

In yet another embodiment, the coated surgical meshes of the invention can be formed to encapsulate a pacemaker, a defibrillator generator, an implantable access system, a neurostimulator, or any other implantable device for the purpose of securing them in position, providing pain relief, inhibiting scarring or fibrosis and/or inhibiting bacterial growth. Such coated meshes formed into an appropriate shape either before or after coating with the biodegradable polymers.

The surgical meshes of the invention can deliver multiple drugs from one or more independent layers.

The invention thus provides a method of delivering drugs at controlled rates and for set durations of time using biodegradable polymers.

DETAILED DESCRIPTION OF THE INVENTION

Figure 1:
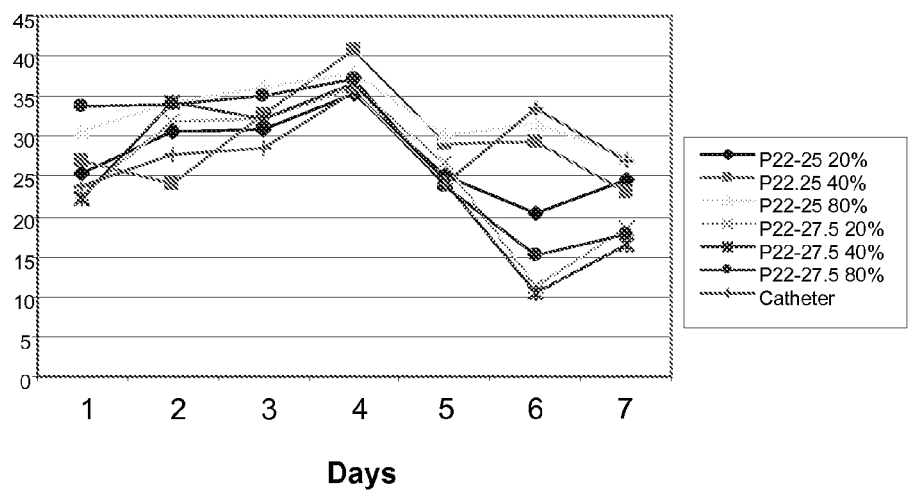
FIG. 1. graphically depicts the zone of inhibition (ZOI) for polyarylate-coated meshes containing rifampin and minocycline hydrochloride that have been incubated on *Staphylococcus aureus* lawns for the indicated times (Example 1). The symbols represent the following meshes: ♦, P22-25 20 passes; ■, P22-25 40 passes; ▲, P22-25 80 passes; x, P22-27.5 20 passes; *, P22-27.5 40 passes; ●, P22-27.5 80 passes; and |, catheter.

The present invention is directed to medical prostheses that comprise a mesh and one or more coating which temporarily stiffen the mesh, preferably by at least 1.1 times its original stiffness. The coatings on such meshes do not alter the integrity of the mesh and thus allow the mesh to remain porous. In general, the coatings do not substantially alter the porosity of the mesh. In some embodiments, the medical prosthesis comprises a mesh with one or more coatings with at least one of the coatings comprising a stiffening agent that coats the filaments or fibers of the mesh so to temporarily immobilize the contact points of those filaments or fibers. Again, the coatings on such meshes do not alter the integrity strength of the underlying mesh. and thus allow the mesh to remain porous after coating. In general, the coatings do not substantially alter the porosity of the mesh. The prostheses of the invention are useful for surgical repair and reconstruction of soft tissue defects.

In one embodiment, the mesh of the medical prostheses can be shaped into a three-dimensional structure, e.g., on a mold or other form, and a coating applied. The coatings (and stiffening agents) have sufficient strength to hold the mesh in that shape once the coating has dried, cured or set, as appropriate to the particular agent, and the mesh removed from the mold or form. Accordingly, the present invention provides medical prostheses that are three dimensional structures with coatings that have temporary stiffness in accordance with the invention as described herein.

A mesh in accordance with the invention is any web or fabric with a construction of knitted, braided, woven or nonwoven filaments or fibers that are interlocked in such a way to create a fabric or a fabric-like material. As used in accordance with the present invention, "mesh" also includes any porous prosthesis suitable for temporarily stiffening.

Surgical meshes are well known in the art and any such mesh can be coated as described herein. The meshes used in the present invention are made from biocompatible materials, synthetic or natural, including but not limited to, polypropylene, polyester, polytetrafluroethylene, polyamides and combinations thereof. One of the advantages of the present invention is that the coatings can be used with any commercially available mesh. A preferred mesh is made from woven polypropylene. Pore sizes of meshes vary. For example the Bard Marlex® mesh has pores of 379+/−143 micrometers or approx. 0.4 mm, whereas the Johnson and Johnson Vypro® mesh has pores of 3058+/−62 micrometers or approx. 3 mm.

The stiffening agents of the invention include hydrogels, biodegradable polymers and any other compound capable of imparting temporary stiffness to the mesh in accordance with the invention. Temporary stiffness means that, relative to the corresponding uncoated mesh material, there is an increase in stiffness when one or more coatings are applied in accordance with the invention. Upon use, those coatings then soften or degrade over time in a manner that causes the mesh to revert back to its original stiffness, revert nearly back to its original stiffness or sufficient close to its original stiffness to provide the desired surgical outcome and the expected patient comfort. To determine if the medical prosthesis has temporary stiffness, the prosthesis can be evaluated in vitro or in vivo. For example, a coating can be applied to the mesh and then the mesh left in a physiological solution for a period of time before measuring its stiffness. The time period of stiffness is controlled by the degradation rate (for biodegradable polymers) or absorption ability (for hydrogels). The time period can vary from days, to weeks or even a few months and is most conveniently determined in vitro. Meshes with that revert to their original stiffness in vitro within a reasonable time (from 1 day to 3-4 months) are considered to be temporarily stiffened. Additionally, animal models can be used to assess temporary stiffness by implanting the mesh and then removing it from the animal and determining if its stiffness had changed. Such in vivo results can be correlated with the in vitro results by those of skill in the art. Methods to measure stiffness of a mesh or a coated mesh are known in the art.

A hydrogel is composed of a network of water-soluble polymer chains. Hydrogels are applied as coatings and dried on the mesh. Upon use, e.g., implantation in the body, the hydrogel absorbs water and become soft (hydrogels can contain over 99% water), thereby increasing the flexibility of the mesh and reverting to the original or near original stiffness of the mesh. Typically, hydrogels possess a degree of flexibility very similar to natural tissue, due to their significant water content. Common ingredients for hydrogels, include e.g. polyvinyl alcohol, sodium polyacrylate, acrylate polymers and copolymers with an abundance of hydrophilic groups.

Meshes can have one or more polymer coatings and can optionally include drugs in the coatings. Meshes with a single coating are useful to improve handling of the mesh during surgical implantation and use. Meshes with drugs can be coated with single or multiple layers, depending on the amount of drug to be delivered, the type of drug and desired release rate. For example, a first coating layer can contain drug, while the second layer coating layer contains either no drug or a lower concentration of drug.

The coated implantable surgical meshes of the invention comprise a surgical mesh and one or more biodegradable polymer coating layers with each coating layer optionally, and independently, further containing a drug. The physical, mechanical, chemical, and resorption characteristics of the coating enhance the clinical performance of the mesh and the surgeon's ability to implant the device without affecting the overall or primary performance characteristics of the mesh, especially when used as a permanent implant in the patient.

These characteristics are accomplished by choosing a suitable coating thickness for the selected biodegradable polymer.

The biodegradable coating deposited onto the surface of the mesh gives the mesh superior handling characteristics relative to uncoated meshes and facilitates surgical insertion because it imparts stiffness to the mesh and thereby improves handling thereof. Over time, however, the coating resorbs, or the stiffening agents degrades or softens, to leave a flexible mesh that provides greater patient comfort without loss of strength.

The surgical mesh can be coated with the biodegradable polymer using standard techniques such as spray or dip coating to achieve a uniform coating having a thickness that provides at least 1.1 to 4.5 and more preferably 1.25 to 2 times the stiffness of the uncoated mesh. In addition, the coating is optimized to provide for a uniform, flexible, non-flaking layer that remains adhered to the mesh throughout the implantation and initial wound healing process. Typically, the polymer coating must maintain its integrity for at least 1 week. Optimal coating solutions are obtained by choosing a biodegradable polymer with a solubility between about 0.01 to about 30% in volatile solvents such as methylene chloride or other chlorinated solvents, THF, various alcohols, or combinations thereof. Additionally, it is preferred to use biodegradable polymers with a molecular weight between about 10,000 and about 200,000 Daltons. Such polymers degrade at rates that maintain sufficient mechanical and physical integrity over about 1 week at 37° C. in an aqueous environment.

Additionally, a biodegradable polymer-coated implantable mesh is described in which the biodegradable polymer layer (i.e., the coating) has a chemical composition that provide relatively good polymer-drug miscibility. The polymer layer can contain between 1-80% drug at room temperature as well as between 1-95%, 2-80%, 2-50%, 5-40%, 5-30%, 5-25% and 10-20% drug or 1, 2, 3, 4, 5, 6, 7, 8, 9, or 10% drug as well as 5% increments from 10-95%, i.e., 10, 15, 20, 25, etc. In one embodiment, the biodegradable polymer coating releases drug for at least 2-3 days. Such release is preferred, for example, when the drug is an analgesic to aide in localized pain management at the surgical site. Such loading and release characteristics can be also be obtains for drug polymer-combinations that do not have good miscibility by using multiple layering techniques.

To achieve an analgesic affect, the anesthetic and/or analgesic should be delivered to the injured tissue shortly after surgery or tissue injury. A drug or drugs for inclusion in the coatings of surgical meshes include, but are not limited to analgesics, anti-inflammatory agents, anesthetics, antimicrobial agents, antifungal agents, NSAIDS, other biologies (including proteins and nucleic acids) and the like. Antimicrobial and antifungal agents can prevent the mesh and/or the surrounding tissue from being colonized by bacteria. One or more drugs can be incorporated into the polymer coatings of the invention.

In another embodiment, a mesh of the invention has a coating comprising an anesthetic such that the anesthetic elutes from the implanted coated mesh to the surrounding tissue of the surgical site for between 1 and 10 days, which typically coincides with the period of acute surgical site pain. In another embodiment, delivery of an antimicrobial drug via a mesh of the invention can create an inhibition zone against bacterial growth and colonization surrounding the implant during the healing process (e.g., usually about 30 days or less) and/or prevent undue fibrotic responses.

Using biodegradable polymer coatings avoids the issue of drug solubility, impregnation or adherence in or to the underlying device since a coating having suitable chemical properties can be deposited onto the mesh, optionally in concert with one or more drugs, to provide for the release of relatively high concentrations of those drugs over extended periods of time. For example, by modulating the chemical composition of the biodegradable polymer coating and the coating methodology, a clinically-efficacious amount of anesthetic drug can be loaded onto a mesh to assure sufficient drug elution and to provide surgical site, post-operative pain relief for the patient.

To provide such post-operative, acute pain relief, the mesh should elute from about 30 mg to about 1000 mg of anesthetic over 1-10 days, including, e.g., about 30, 50, 100, 200, 400, 500, 750 or 1000 mg over that time period.

The prosthesis should elute clinically effective amounts of anesthetic during the acute post-operative period when pain is most noticeable to the patient. This period, defined in several clinical studies, tends to be from 12 hours to 5 days after the operation, with pain greatest around 24 hours and subsiding over a period of several days thereafter. Prior to 12 hours, the patient is usually still under the influence of any local anesthetic injection given during the surgery itself. After the 5-day period, most of the pain related to the surgery itself (i.e., incisional pain and manipulation of fascia, muscle, & nerves) has resolved to a significant extent.

Bupivacaine has a known toxicity profile, duration of onset, and duration of action. Drug monographs recommend the daily dose not to exceed 400 mg. Those of skill in the art can determine the amount of anesthetic to include in a polymer coating or a hydrogel coating to achieve the desired amount and duration of pain relief.

There are numerous reports of reduction or complete elimination of narcotic use and pain scores after open hernia repair during days 2-5 with concomitant use of catheter pain pump system. In these cases, the pump delivers either a 0.25% or 0.5% solution of bupivacaine to the subfascial area (Sanchez, 2004; LeBlanc, 2005; and Lau, 2003). At a 2 mL/hour flow rate, this translates into constant "elution" of approximately 120 mg of bupivacaine per day. However, this system purportedly suffers from leakage, so the 120 mg per day may only serve as an extremely rough guide for the amount of bupivacaine that should be delivered to provide adequate post-operative pain relief.

One of the most well characterized sustained release depot systems for post-operative pain relief reported in the literature is a PLGA microsphere-based sustained release formulation of bupivacaine. This formulation was developed and tested in humans for relief of subcutaneous pain as well as neural blocks. Human trials indicated that subcutaneous pain was relieved via injection of between 90 to 180 mg of bupivacaine which then eluted into the surrounding tissue over a 7-day period, with higher concentrations in the initial 24-hour period followed by a gradual taper of the concentration. Other depot sustained release technologies have successfully suppressed post-operative pain associated with inguinal hernia repair. For example, external pumps and PLGA microsphere formulations have each purportedly release drug for approximately 72 hours.

To achieve loading at the lower limit of the elution profile, for example, one can choose a relatively hydrophilic biodegradable polymer and combines it with the anesthetic hydrochloride salt so that the anesthetic dissolves in the polymer at a concentration below the anesthetic's saturation limit. Such a formulation provides non-burst release of anesthetic. To achieve loading at the upper limit of the elution profile, one can spray coat a layer of an anesthetic-polymer mixture that contains the anesthetic at a concentration above its saturation limit. In this formulation, the polymer does not act as a control mechanism for release of the anesthetic, but rather acts as a binder to hold the non-dissolved, anesthetic particles together and alters the crystallization kinetics of the drug. A second coating layer, which may or may not contain further anesthetic, is sprayed on top of the first layer. When present in the second coating, the anesthetic concentration is at a higher ratio of polymer to anesthetic, e.g., a concentration at which the anesthetic is soluble in the polymer layer.

The top layer thus can serve to control the release of the drug in the bottom layer (aka depot layer) via the drug-polymer solubility ratio. Moreover, it is possible to alter the release rate of the drug by changing the thickness of the polymer layer and changing the polymer composition according to its water uptake. A polymer that absorbs a significant amount of water within 24 hours will release the contents of the depot layer rapidly. However, a polymer with limited water uptake or variable water uptake (changes as a function of its stage of degradation) will retard release of the water soluble anesthetic agent.

Biodegradable polymers suitable for coatings of the invention include but are not limited to, polylactic acid, polyglycolic acid and copolymers and mixtures thereof such as poly (L-lactide) (PLLA), poly(D,L-lactide) (PLA);

polyglycolic acid [polyglycolide (PGA)], poly(L-lactide-co-D,L-lactide) (PLLA/PLA), poly(L-lactide-co-glycolide) (PLLA/PGA), poly(D,L-lactide-co-glycolide) (PLA/PGA), poly(glycolide-co-trimethylene carbonate) (PGA/PTMC), poly(D,L-lactide-co-caprolactone) (PLA/PCL), poly(glycolide-co-caprolactone) (PGA/PCL), poly(oxa)ester;

polyethylene oxide (PEO), polydioxanone (PDS), polypropylene fumarate, poly(ethyl glutamate-co-glutamic acid), poly(tert-butyloxy-carbonylmethyl glutamate), polycaprolactone (PCL), polycaprolactone co-butylacrylate, polyhydroxybutyrate (PHBT) and copolymers of polyhydroxybutyrate, poly(phosphazene), poly(phosphate ester), poly(amino acid) and poly(hydroxy butyrate), polydepsipeptides, maleic anhydride copolymers, polyphosphazenes, polyiminocarbonates, poly[(97.5% dimethyl-trimethylene carbonate)-co-(2.5% trimethylene carbonate)], poly(orthoesters), tyrosine-derived polyarylates, tyrosine-derived polycarbonates and tyrosine-derived polyphosphonates, PEG derivatives, polyethylene oxide, hydroxypropylmethylcellulose, polysaccharides such as hyaluronic acid, chitosan and regenerate cellulose, and proteins such as gelatin and collagen, and mixtures and copolymers thereof, among others.

Methods of making biodegradable polymers are well known in the art.

The preferred biodegradable polymers of the invention have tyrosine-derived diphenol monomer units that are copolymerized with the appropriate chemical moiety to form a polyarylate, a polycarbonate, a polyiminocarbonate, a polyphosphonate or any other.

The preferred biodegradable polymers are tyrosine-based polyarylates including those described in U.S. Pat. Nos. 4,980,449; 5,099,060; 5,216,115; 5,317,077; 5,587,507; 5,658,995; 5,670,602; 6,048,521; 6,120,491; 6,319,492; 6,475,477; 6,602,497; 6,852,308; 7,056,493; RE37,160E; and RE37,795E; and as well as U.S. Patent Application Publication Nos. 2002/0151668; 2003/0138488; 2003/0216307; 2004/0254334; 2005/0165203; and as well as PCT Publication Nos. WO99/52962; WO 01/49249; WO 01/49311; WO03/091337. These patents and publications also disclose other polymers containing tyrosine-derived diphenol monomer units, including polyarylates, polycarbonates, polyiminocarbonates, polythiocarbonates, polyphosphonates and polyethers. Likewise, the foregoing patents and publications describe methods for making these polymers, some methods of which may be applicable to synthesizing other biodegradable polymers. Finally, the foregoing patents and publications also describe blends and copolymers with polyalkylene oxide, including polyethylene glycol (PEG). All such polymers are contemplated for use in the present invention.

The representative structures for the foregoing polymers are provide in the above-cited patents and publications which are incorporated herein by reference.

As used herein, DTE is the diphenol monomer desaminotyrosyl-tyrosine ethyl ester; DTBn is the diphenol monomer desaminotyrosyl-tyrosine benzyl ester; DT is the corresponding free acid form, namely desaminotyrosyl-tyrosine. BTE is the diphenol monomer 4-hydroxy benzoic acid-tyrosyl ethyl ester; BT is the corresponding free acid form, namely 4-hydroxy benzoic acid-tyrosine.

P22 is a polyarylate copolymer produced by condensation of DTE with succinate. P22-10, P22-15, P22-20, P22-xx, etc., represents copolymers produced by condensation of (1) a mixture of DTE and DT using the indicated percentage of DT (i.e., 10, 15, 20 and xx % DT, etc.) with (2) succinate.

Additional preferred polyarylates are random copolymer of desaminotyrosyl-tyrosine (DT) and an desaminotyrosyl-tyrosyl ester (DT ester), wherein the copolymer comprises from about 0.001% DT to about 80% DT and the ester moiety can be a branched or unbranched alkyl, alkylaryl, or alkylene ether group having up to 18 carbon atoms, any group of which can, optionally have a polyalkylene oxide therein. Similarly, another group of polyarylates are the same as the foregoing but the desaminotyrosyl moiety is replaced by a 4-hydroxybenzoyl moiety. Preferred DT or BT contents include those copolymers with from about 1% to about 30%, from about 5% to about 30% from about 10 to about 30% DT or BT. Preferred diacids (used informing the polyarylates) include succinate, glutarate and glycolic acid.

Additional biodegradable polymers useful for the present invention are the biodegradable, resorbable polyarylates and polycarbonates disclosed in U.S. provisional application Ser. No. 60/733,988, filed Nov. 3, 2005 and in its corresponding PCT Appln. No. PCT/US06/42944, filed Nov. 3, 2006. These polymers, include, but are not limited to, BTE glutarate, DTM glutarate, DT propylamide glutarate, DT glycineamide glutarate, BTE succinate, BTM succinate, BTE succinate PEG, BTM succinate PEG, DTM succinate PEG, DTM succinate, DT N-hydroxysuccinimide succinate, DT glucosamine succinate, DT glucosamine glutarate, DT PEG ester succinate, DT PEG amide succinate, DT PEG ester glutarate and DT PEG ester succinate.

The most preferred polyarylates are the DTE-DT succinate family of polymers, e.g., the P22-xx family of polymers having from 0-50%, 5-50%, 5-40%, 1-30% or 10-30% DT, including but not limited to, about 1, 2, 5, 10, 15, 20, 25, 27.5, 30, 35, 40%, 45% and 50% DT.

Additionally, the polyarylate polymers used in the present invention can have from 0.1-99.9% PEG diacid to promote the degradation process as described in U.S. provisional application Ser. No. 60/733,988.

The prostheses of the invention can be used to reconstruct, reinforce, bridge, replace, repair, support, stabilize, position or strengthen any soft tissue defect.

For example, soft tissue defects that can be treated in accordance with the instant invention include hernias, including but not limited to inguinal, femoral, umbilical, abdominal, incisional, intramuscular, diphragmatic, abdomino-throacic and thoracic hernias. The prosetheses of the invention can also be used for structural reinforcement for muscle flaps, to provide vascular integrity, for ligament repair/replacement and for organ support/positioning/repositioning such as done with a bladder sling, a breast lift, or an organ bag/wrap. The prostheses of the invention can be used in recontruction procedures involving soft tissue such as an orthopaedic graft support/stabilization, as supports for reconstructive surgical grafts and as supports for bone fractures.

Examples of drugs suitable for use with the present invention include anesthetics, antibiotics (antimicrobials), anti-inflammatory agents, fibrosis-inhibiting agents, anti-scarring agents, leukotriene inhibitors/antagonists, cell growth inhibitors and the like. As used herein, "drugs" is used to include all types of therapeutic agents, whether small molecules or large molecules such as proteins, nucleic acids and the like. Those of skill in the art can readily determine the amount of a particular drug to include in the coatings on the meshes of the invention.

Any pharmaceutically acceptable form of the drugs of the present invention can be employed in the present invention, e.g., the free base or a pharmaceutically acceptable salt or ester thereof. Pharmaceutically acceptable salts, for instance, include sulfate, lactate, acetate, stearate, hydrochloride, tartrate, maleate, citrate, phosphate and the like.

Examples of non-steroidal anti-inflammatories include, but are not limited to, naproxen, ketoprofen, ibuprofen as well as diclofenac; celecoxib; sulindac; diflunisal; piroxicam; indomethacin; etodolac; meloxicam; r-flurbiprofen; mefenamic; nabumetone; tolmetin, and sodium salts of each of the foregoing; ketorolac bromethamine; ketorolac bromethamine tromethamine; choline magnesium trisalicylate; rofecoxib; valdecoxib; lumiracoxib; etoricoxib; aspirin; salicylic acid and its sodium salt; salicylate esters of alpha, beta, gamma-tocopherols and tocotrienols (and all their d, 1, and racemic isomers); and the methyl, ethyl, propyl, isopropyl, n-butyl, sec-butyl, t-butyl, esters of acetylsalicylic acid.

Examples of anesthetics include, but are not limited to, licodaine, bupivacaine, and mepivacaine. Further examples of analgesics, anesthetics and narcotics include, but are not limited to acetaminophen, clonidine, benzodiazepine, the benzodiazepine antagonist flumazenil, lidocaine, tramadol, carbamazepine, meperidine, zaleplon, trimipramine maleate, buprenorphine, nalbuphine, pentazocain, fentanyl, propoxyphene, hydromorphone, methadone, morphine, levorphanol, and hydrocodone.

Examples of antimicrobials include, but are not limited to, triclosan, chlorhexidine, rifampin, minocycline, vancomycin, gentamycine, cephalosporins and the like. In preferred embodiments the coatings contain rifampin and another antimicrobial agent. In another preferred embodiment, the coatings contains a cephalosporin and another antimicrobial agent. Preferred combinations include rifampin and minocycline, rifampin and gentamycin, and rifampin and minocycline.

Further antimicrobials include aztreonam; cefotetan and its disodium salt; loracarbef; cefoxitin and its sodium salt; cefazolin and its sodium salt; cefaclor; ceftibuten and its sodium salt; ceftizoxime; ceftizoxime sodium salt; cefoperazone and its sodium salt; cefuroxime and its sodium salt; cefuroxime axetil; cefprozil; ceftazidime; cefotaxime and its sodium salt; cefadroxil; ceftazidime and its sodium salt; cephalexin; cefamandole nafate; cefepime and its hydrochloride, sulfate, and phosphate salt; cefdinir and its sodium salt; ceftriaxone and its sodium salt; cefixime and its sodium salt; cefpodoxime proxetil; meropenem and its sodium salt; imipenem and its sodium salt; cilastatin and its sodium salt; azithromycin; clarithromycin; dirithromycin; erythromycin and hydrochloride, sulfate, or phosphate salts ethylsuccinate, and stearate forms thereof; clindamycin; clindamycin hydrochloride, sulfate, or phosphate salt; lincomycin and hydrochloride, sulfate, or phosphate salt thereof; tobramycin and its hydrochloride, sulfate, or phosphate salt; streptomycin and its hydrochloride, sulfate, or phosphate salt; vancomycin and its hydrochloride, sulfate, or phosphate salt; neomycin and its hydrochloride, sulfate, or phosphate salt; acetyl sulfisoxazole; colistimethate and its sodium salt; quinupristin; dalfopristin; amoxicillin; ampicillin and its sodium salt; clavulanic acid and its sodium or potassium salt; penicillin G; penicillin G benzathine, or procaine salt; penicillin G sodium or potassium salt; carbenicillin and its disodium or indanyl disodium salt; piperacillin and its sodium salt; ticarcillin and its disodium salt; sulbactam and its sodium salt; moxifloxacin; ciprofloxacin; ofloxacin; levofloxacins; norfloxacin; gatifloxacin; trovafloxacin mesylate; alatrofloxacin mesylate; trimethoprim; sulfamethoxazole; demeclocycline and its hydrochloride, sulfate, or phosphate salt; doxycycline and its hydrochloride, sulfate, or phosphate salt; minocycline and its hydrochloride, sulfate, or phosphate salt; tetracycline and its hydrochloride, sulfate, or phosphate salt; oxytetracycline and its hydrochloride, sulfate, or phosphate salt; chlortetracycline and its hydrochloride, sulfate, or phosphate salt; metronidazole; dapsone; atovaquone; rifabutin; linezolide; polymyxin B and its hydrochloride, sulfate, or phosphate salt; sulfacetamide and its sodium salt; and clarithromycin.

Examples of antifungals include amphotericin B; pyrimethamine; flucytosine; caspofungin acetate; fluconazole; griseofulvin; terbinafin and its hydrochloride, sulfate, or phosphate salt; ketoconazole; micronazole; clotrimazole; econazole; ciclopirox; naftifine; and itraconazole.

Other drugs that can be incorporated into surgical meshes include, but are not limited to, keflex, acyclovir, cephradine, malphalen, procaine, ephedrine, adriamycin, daunomycin, plumbagin, atropine, quinine, digoxin, quinidine, biologically active peptides, cephradine, cephalothin, cis-hydroxy-L-proline, melphalan, penicillin V, aspirin, nicotinic acid, chemodeoxycholic acid, chlorambucil, paclitaxel, 5-flurouracil and the like.

Examples of useful proteins include cell growth inhibitors such as epidermal growth factor.

Examples of anti-inflammatory compound include, but are not limited to, anecortive acetate; tetrahydrocortisol, 4,9(11)-pregnadien-17.alpha.,21-diol-3,20-dione and its -21-acetate salt; 11-epicortisol; 17.alpha.-hydroxyprogesterone; tetrahydrocortexolone; cortisona; cortisone acetate; hydrocortisone; hydrocortisone acetate; fludrocortisone; fludrocortisone acetate; fludrocortisone phosphate; prednisone; prednisolone; prednisolone sodium phosphate; methylprednisolone; methylprednisolone acetate; methylprednisolone, sodium succinate; triamcinolone; triamcinolone-16,21-diacetate; triamcinolone acetonide and its -21-acetate, -21-disodium phosphate, and -21-hemisuccinate forms; triamcinolone benetonide; triamcinolone hexacetonide; fluocinolone and fluocinolone acetate; dexamethasone and its 21-acetate, -21-(3,3-dimethylbutyrate), -21-phosphate disodium salt, -21-diethylaminoacetate, -21-isonicotinate, -21-dipropionate, and -21-palmitate forms; betamethasone and its -21-acetate, -21-adamantoate, -17-benzoate, -17,21-dipropionate, -1 7-valerate, and -21-phosphate disodium salts; beclomethasone; beclomethasone dipropionate; diflorasone; diflorasone diacetate; mometasone furoate; and acetazolamide.

Those of ordinary skill in the art will appreciate that any of the foregoing disclosed drugs can be used in combination or mixture in coatings of the present invention.

Methods

Another aspect of the invention is directed to a process for coating a mesh with a stiffening agent that coats the filaments or fibers of the mesh to temporarily immobilize contact points of the filaments or fibers of said mesh. The method is comprises (a) preparing a coating solution comprising a solvent and said stiffening agent; (b) spraying a mesh one or more times to provide an amount of said solution on said mesh to produce a coating having a thickness and placement sufficient to temporarily immobilize contact points of the filaments or fibers of said mesh that coats filaments or fibers; and (c) drying said mesh to produce said coating. An example of ratio of coating thickness to polymer coating is shown in the scanning electron micrograph of FIG. 7. When used with a drug (or combination of drugs), the drug is included in the coating solution at the desired concentration.

Spraying can be accomplished by known methods. For example, the coating can be applied to the entire mesh or to that portion of the mesh necessary to stiffen it. One technique is to dip the mesh in the coating material; another is to push the mesh through rollers that transfer the coating on the mesh. Spraying the mesh with a microdroplets is also effective. Techniques for selectively coating only those areas necessary to stiffen the mesh include deposition the coating through a template that exposes only the desired areas of coverage for the coating, including dispensing the coating with micro needles or similar means. More preferably the coating can be applied using a photoresist-like mask that expose the desired portions, applying the coating over the photomask and the removing the photomask.

Still another aspect of the invention relates to a method for producing a shaped or three-dimensional medical prosthesis mesh by forming a mesh into a desired shape or three-dimensional shape. This step can be accomplished with the aid of a mold or other form on which to affix and shape the mesh or by holding the mesh in a frame in the desired shape or structural configuration. Once configured into the desired shape, a stiffening agent of the invention is applied to the mesh to coat filaments or fibers and the agent is allowed to dry, set or cure as appropriate, causing the mesh stiffen and hold the desired shape. The mesh is then removed or released from the mold, form or device that had been holding the mesh to produce the three dimensional medical prosthesis which is capable of retaining its shape without any further structural support or aid.

It will be appreciated by those skilled in the art that various omissions, additions and modifications may be made to the invention described above without departing from the scope of the invention, and all such modifications and changes are intended to fall within the scope of the invention, as defined by the appended claims. All references, patents, patent applications or other documents cited are herein incorporated by reference in their entirety.

Example 1

Antibiotic Release from DTE-DT Succinate Coated Mesh

A. Preparation of Mesh by Spray-Coating

A 1% solution containing a ratio of 1:1:8 rifampin:minocycline:polymer in 9:1 tetrahydrofuran/methanol was spray-coated onto a surgical mesh by repeatedly passing the spray nozzle over each side of the mesh until each side was coated with at least 10 mg of antimicrobial-embedded polymer. Samples were dried for at least 72 hours in a vacuum oven before use.

The polymers are the polyarylates P22-xx having xx being the % DT indicated in Table 1. In Table 1, Rxx or Mxx indicates the percentage by weight of rifampin (R) or minocycline (M) in the coating, i.e., R10M10 means 10% rifampin and 10% minocycline hydrochloride with 80% of the indicated polymer. Table 1 provides a list of these polyarylates with their % DT content, exact sample sizes, final coating weights and drug coating weights.

TABLE 1

Polyarylate Coated Meshes with Rifampin and Minocycline HCl

| Sample No. | Coating Parameters | (No. Spray Passes) | Avg. Coating Wt. per 116 cm$^2$ (mg) | Coating Wt. per cm$^2$ (mg) | Rifampin (µg) | Minocycline HCl (µg) |
|---|---|---|---|---|---|---|
| 1 | P22-25 | R10M10 (20) | 100 | 0.86 | 86 | 86 |
| 2 | P22-25 | R10M10 (40) | 150 | 1.29 | 129 | 129 |
| 3 | P22-25 | R10M10 (80) | 200 | 1.72 | 172 | 172 |
| 4 | P22-27.5 | R10M10 (1) | 20 | 0.17 | 17 | 17 |
| 5 | P22-27.5 | R10M10 (2) | 40 | 0.34 | 34 | 34 |
| 6 | P22-27.5 | R10M10 (3) | 60 | 0.52 | 52 | 52 |

B. Zone of Inhibition (ZOI) Studies

The ZOI for antibiotic coated meshes was determined according to the Kirby-Bauer method. *Staphylococcus epidermidis* or *Staphylococcus aureus* were inoculated into Triplicate Soy Broth (TSB) from a stock culture and incubated at 37° C. until the turbidity reached McFarland #0.5 standard (1-2 hours). Plates were prepared by streaking the bacteria onto on Mueller-Hinton II agar (MHA) three times, each time swabbing the plate from left to right to cover the entire plate and rotating the plate between swabbing to change direction of the streaks.

A pre-cut piece (1-2 cm$^2$) of spray-coated mesh was firmly pressed into the center of pre-warmed Mueller Hinton II agar plates and incubated at 37° C. Pieces were transferred every 24 h to fresh, pre-warmed Mueller Hinton II agar plates using sterile forceps. The distance from the sample to the outer edge of the inhibition zone was measured every 24 h and is reported on the bottom row in Table 2 and 3 for each sample. The top row for each sample represents difference between the diameter of the ZOI and the diagonal of the mesh. Table 2 shows the ZOI results for meshes placed on *S. epidermidis* lawns and Table 3 shows the ZOI results for meshes placed on *S. aureus* lawns. Additionally, three pieces were removed every 24 h for analysis of residual minocycline and rifampin.

FIG. 1 shows the total ZOI on *S. aureus* for meshes with 10% each of minocycline hydrochloride and rifampin in a DTE-DT succinate polyarylate coating having 25% or 27.5% DT. The catheter is a COOK SPECTRUM venous catheter impregnated with rifampin and minocycline hydrochloride.

TABLE 2

S. epidermidis ZOI

| Sample No. | Coating Parameters | | Day 1 (mm) | Day 2 (mm) | Day 3 (mm) | Day 4 (mm) | Day 6 (mm) | Day 7 (mm) |
|---|---|---|---|---|---|---|---|---|
| 1 | P22-25 | R10M10 | 18.65 | 31.70 | 33.04 | 29.63 | 25.43 | 15.66 |
|   |        |        | 31.30 | 44.36 | 45.70 | 42.29 | 38.08 | 28.31 |
| 2 | P22-25 | R10M10 | 19.28 | 30.59 | 33.67 | 31.74 | 0.60  | 8.56  |
|   |        |        | 32.10 | 43.45 | 46.53 | 44.60 | 13.45 | 21.42 |
| 3 | P22-25 | R10M10 | 26.59 | 34.70 | 30.31 | 31.75 | 23.65 | 17.29 |
|   |        |        | 39.48 | 47.59 | 43.20 | 46.16 | 36.54 | 30.18 |
| 4 | P22-27.5 | R10M10 | 18.33 | 31.58 | 35.25 | 30.45 | 2.08  | 6.72  |
|   |        |        | 31.06 | 44.31 | 47.98 | 43.18 | 14.81 | 19.45 |
| 5 | P22-27.5 | R10M10 | 17.48 | 32.81 | 33.68 | 28.06 | 7.89  | 12.86 |
|   |        |        | 30.17 | 45.51 | 46.38 | 40.76 | 20.59 | 25.56 |
| 6 | P22-27.5 | R10M10 | 31.73 | 29.81 | 35.03 | 24.99 | 12.55 | 16.22 |
|   |        |        | 44.42 | 42.50 | 47.72 | 37.68 | 25.24 | 28.91 |

TABLE 3

S. aureus ZOI

| Sample No. | Coating Parameters | | Day 1 (mm) | Day 2 (mm) | Day 3 (mm) | Day 4 (mm) | Day 5 (mm) | Day 7 (mm) |
|---|---|---|---|---|---|---|---|---|
| 1 | P22-25 | R10M10 | 12.75 | 17.90 | 18.22 | 22.44 | 12.35 | 11.94 |
|   |        |        | 25.84 | 30.66 | 30.97 | 35.20 | 25.11 | 24.69 |
| 2 | P22-25 | R10M10 | 14.23 | 11.28 | 20.04 | 28.24 | 16.31 | 10.35 |
|   |        |        | 26.90 | 23.94 | 32.71 | 40.91 | 28.98 | 23.02 |
| 3 | P22-25 | R10M10 | 17.87 | 21.52 | 23.45 | 25.36 | 17.42 | 14.72 |
|   |        |        | 30.57 | 34.22 | 36.15 | 36.02 | 30.12 | 27.42 |
| 4 | P22-27.5 | R10M10 | 9.77  | 19.02 | 19.06 | 23.01 | 13.81 | 5.61  |
|   |        |        | 22.76 | 32.01 | 32.05 | 36.00 | 26.80 | 18.6  |
| 5 | P22-27.5 | R10M10 | 9.70  | 21.77 | 19.55 | 24.00 | 11.84 | 3.89  |
|   |        |        | 22.30 | 34.36 | 35.48 | 36.60 | 24.44 | 16.49 |
| 6 | P22-27.5 | R10M10 | 20.92 | 21.29 | 22.40 | 24.27 | 11.06 | 4.99  |
|   |        |        | 33.68 | 34.05 | 35.15 | 37.02 | 23.82 | 17.75 |

Table 4 shows that the duration of in vitro drug release increases with the hydrophilicity of the resorbable polymer. Solvent cast films were soaked in PBS and antibiotic release was monitored by HPLC.

TABLE 4

Antibiotic Release as a Function of Polymer Hydrophilicity

| Films | | Days releasing Rifampin | Days releasing MinocyclineHCl |
|---|---|---|---|
| P22-15 | R10M10 | 32 | 32 |
| P22-20 | R10M10 | 25 | 25 |
| P22-25 | R10M10 | 7 | 7 |
| P22-27.5 | R10M10 | 10 | 10 |
| P22-30 | R10M10 | 4 | 4 |

Example 2

Bupivacaine Release from DTE-DT Succinate Coated Mesh

A. Preparation of Mesh

Figure 2:
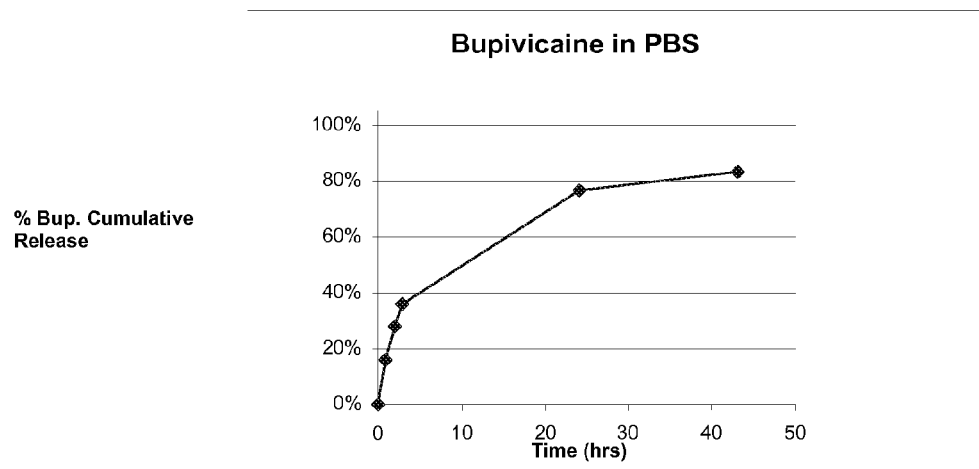
FIG. 2 graphically depicts cumulative bupivacaine release from multilayer polyarylate-coated meshes.

For the experiment shown in FIG. 2, a first depot coating containing 540 mg of bupivacaine HCl as a 4% solution with 1% P22-27.5 polyarylate in a mixture of THF Methanol was spray coated onto a mesh. A second layer consisting of 425 mg of the same polyarylate alone was deposited on top of the first layer.

Figure 3:
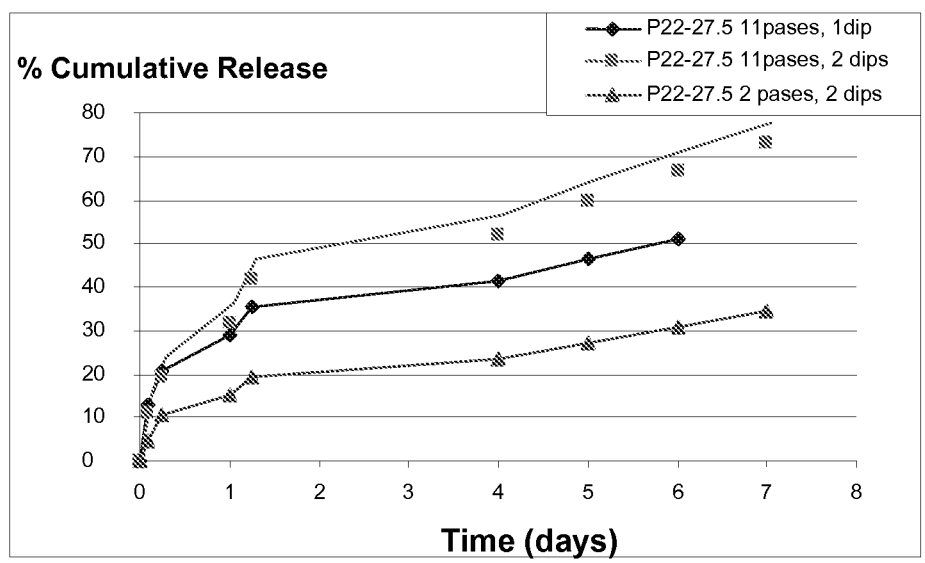
FIG. 3 graphically depicts cumulative bupivacaine release from multilayer polyarylate-coated meshes having various loadings of bupivacaine. The symbols represent the following meshes: ♦, P22-27.5 (11 passes, 1 dip); ■, P22-27.5 (11 passes, 2 dips); and ▲, P22-27.5 (2 passes, 2 dips).

For the experiment shown in FIG. 3, a solution of approximately 4% bupivacaine in DTE-DT succinate polymer having 27.5% DT was sprayed onto a mesh using the indicted number of passes followed by the indicated number of dips into a solution of the same polyarylate in THF:Methanol (9:1)

B. Anesthetic Release

Pre-weighed pieces of mesh were placed in PBS at 37° C. and a sample withdrawn periodically for determination of bupivacaine by HPLC. FIG. 2 shows the cumulative release of bupivacaine into PBS from the multilayer polyarylate coating as a function of time. Nearly 80% of the bupivacaine had been released after 25 hours of incubation.

FIG. 3 is an example of the changes in release characteristics that can be achieved by altering both the amount of drug in the depot layer and the thickness of the outer layer. These coated surgical meshes are much stiffer than their uncoated counterparts.

Example 3

In Vivo Bupivacaine Release from DTE-DT Succinate Coated Meshes

A. Overview

Rats with jugular cannulas for pharmacokinetic studies were surgically implanted with a 1×2 cm P22-27.5 polyarylate-coated mesh containing 7.5 mg of bupivacaine/cm$^2$. Before surgery, baseline pin-prick responses to nociception were measured at the planned surgical incision site, and baseline blood samples were obtained. A hernia was created by incision into the peritoneal cavity during via subcostal laparotomy, and a Lichtenstein non-tension repair was performed using the bupivacaine-impregnated polyarylate-coated mesh. Blood samples were drawn at 3, 6, 24, 48, 72, 96, and 120 hours after implantation. Prior to drawing blood, the rats were subjected to a pin prick test to assess dermal anesthesia from bupivacaine release. The behavioral results indicate that moderate levels of dermal anesthesia appeared from 3 to 120 hours, with the amount at 6 and 48 hours significantly above baseline ($p<0.05$). Pharmacokinetic analysis indicates that the plasma bupivacaine levels fit a one-compartment model with first-order absorption from 0 to 24 hours.

B. Preparation of Surgical Mesh

A polypropylene mesh was spray coated as described in the first paragraph of Example 2. Individual meshes were cut to 1×2 cm, individually packaged, and sterilized by gamma irradiation. The mesh was loaded with 7.5 mg/cm$^2$ of bupivacaine HCl for a total of 15 mg of bupivacaine loaded per 1×2 cm mesh.

C. Surgical Implantation of Mesh

Eight male rats, 59-63 days old and weighing from 250-275 g, were obtained from Taconic Laboratory (Germantown, N.Y.) with an external jugular cannula (SU007). Each rat was anesthetized with isoflurane to a plane of surgical anesthesia, as determined by the absence of a response to toe pinch and corneal reflex and maintained at 2% isoflurane during surgery. The subcostal site was shaved, washed with 10% providone iodine and rinsed with 70% ethanol. Sterile drapes were used to maintain an aseptic surgical field, and sterilized instruments were re-sterilized between rats using a hot-bead sterilizer. A 2.5 cm skin incision was made 0.5 cm caudal to and parallel to the last rib. The underlying subcutaneous space (1 cm on both sides of the incision) was loosened to accommodate the mesh. A 2 cm incision was made through the muscle layers along the same plane as the skin incision, penetrating the peritoneal cavity and the peritoneum was closed with 6-0 Prolene sutures in a continuous suture pattern. Rather than suturing the inner and outer oblique muscles using the classic "tension closure," a Lichtenstein "non-tension" repair was undertaken using the mesh as the repair material. The mesh prepared in Section A was positioned over the incisional hernia, and sutured into the internal and external oblique muscles using 6-0 Prolene sutures. The subcutaneous tissue was then sutured in a continuous pattern with 6 to 8 6-0 Prolene sutures to prevent the rats from accessing the mesh, followed by 6 to 8 skin sutures. Total surgical time was 10 min for anesthetic induction and preparation and 20 min for the surgery.

The rats were allowed to recover in their home cages, and monitored post-surgically until they awoke. Blood samples were drawn for determination of plasma bupivacaine levels at 3, 6, 24, 48, 72, 96, and 120 hours after surgery. The rats were assessed for guarding the incision, and the incision was assessed for signs of inflammation, swelling or other signs of infection. No rats exhibited toxicity or seizures, or were in a moribund state from infection or the release of bupivacaine.

D. Dermal Anesthetic Tests

The nociceptive pin prick test was used to assess dermal anesthesia (Morrow and Casey, 1983; Kramer et al., 1996; Haynes et al., 2000; Khodorova and Strichartz, 2000). Holding the rat in one hand, the other hand was used to apply the pin. Nociception was indicated by a skin-flinch or by a nocifensive (i.e., startle or attempt to escape) response from the rat. While the presence of the mesh interfered with the skin flinch response, nocifensive response remained completely intact.

Figure 4:
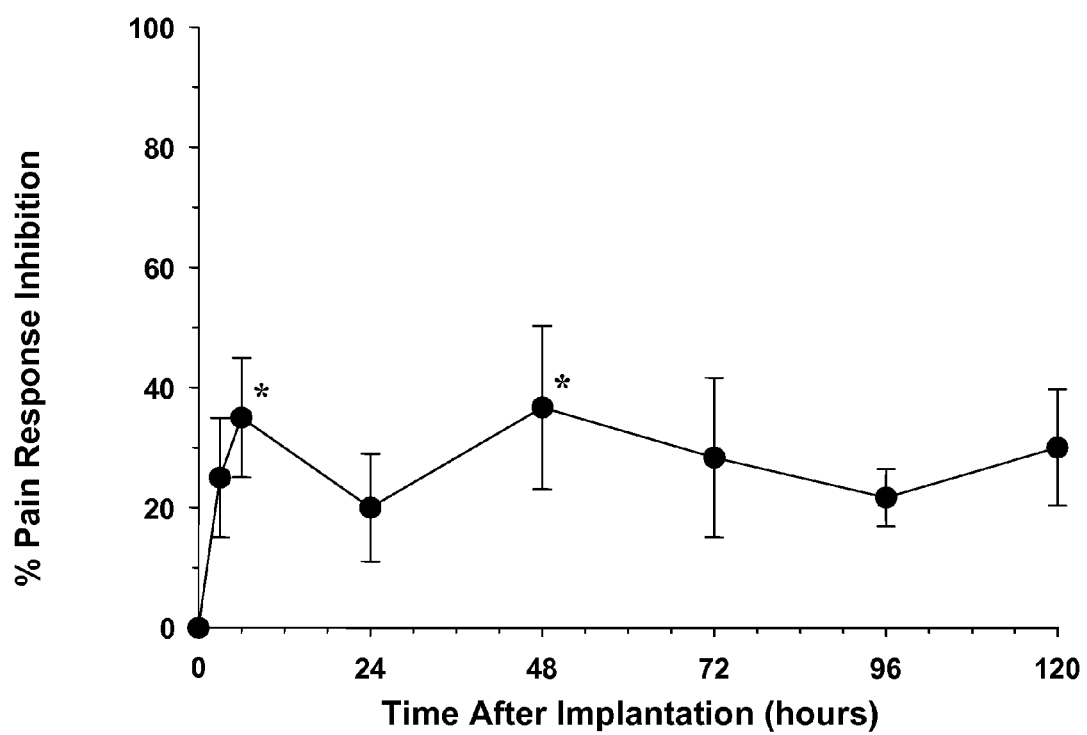
FIG. 4 graphically depicts the time course of dermal anesthesia from 1×2 cm surgically implanted, polyarylate meshes containing 7.5 mg/cm$^2$ bupivacaine. Meshes were implanted in rats by subcostal laparotomy, pin-prick responses were determined and are shown as % pain response inhibition (see Examples for details). The "*" indicates statistically significant response at $p<0.05$ compared to the baseline pin-prick response.
Figure 5:
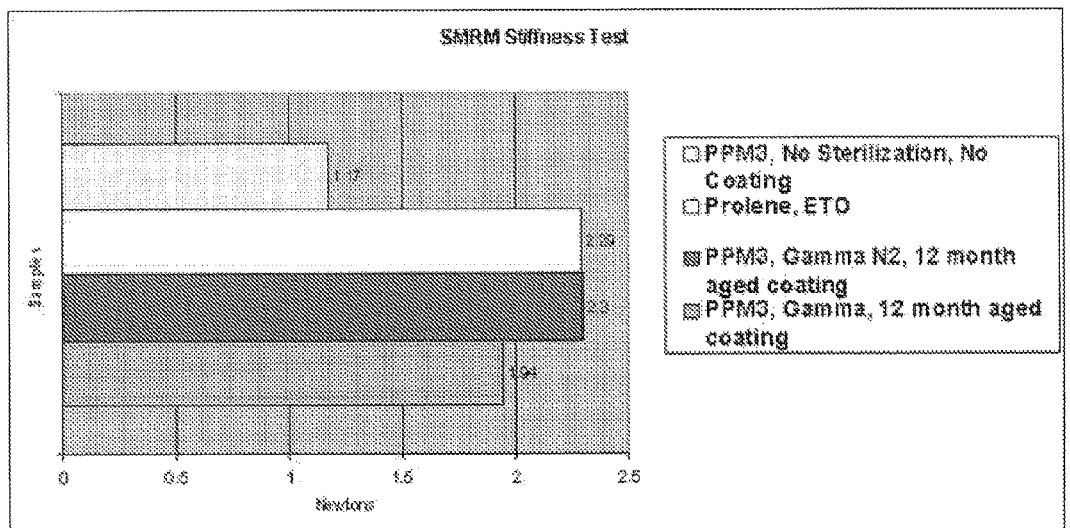
FIG. 5 graphically depicts mesh stiffness. The bars, from top to bottom, represent the stiffness for (1) a PPM3 mesh without a polyarylate coating and without sterilization, (2) a Prolene™ (Ethicon) mesh sterilized with ethylene oxide, (3) a polyarylate-coated PPM3 mesh 12 months after coating and sterilized by gamma irradiation with a nitrogen flush, and (4) a polyarylate-coated PPM3 mesh 12 months after coating and sterilized by gamma irradiation.

Baseline nocifensive responses to 10 applications of the pin from a Buck neurological hammer were obtained at the planned incision site prior to mesh implantation. After surgery, the pin prick test was applied rostral to the incision. The nerves caudal to the incision were transected during the procedure, and therefore did not respond to pin application and were not tested. The post-implantation test was repeated using the same force as before surgery and with 10 pin applications, and the percent inhibition of nocifensive responding was calculated by: [1−(test responses/10 base responses)]× 100. The data was analyzed using repeated measures ANOVA followed by post hoc analysis using the Tukey's test. The results are shown in FIG. 4.

Example 4

Mesh Stiffness

A. Meshes prepared as described in Example 1 were subject to stiffness testing according to the method of TyRx Pharma Inc. Mesh Stiffness Test Protocol, ATM 0410, based on ASTM 4032-94. Meshes were sealed in foil bags before sterilization using gamma irradiation. Where indicated by "Gamma $N_2$", the bags were flushed with nitrogen before sealing and irradiation. Meshes were tested in triplicate. The results are shown in Table 5 and indicate that aging does not affect the flexibility of the coated meshes.

TABLE 5

Stiffness Testing

| Mesh | Sample 1 (Newtons) | Sample 2 (Newtons) | Sample 3 (Newtons) | Average (Newtons) | t-test |
|---|---|---|---|---|---|
| PPM3, Gamma, 12 month aged coating | 1.84 | 2.36 | 1.62 | 1.94 | 0.016 |
| PPM3, Gamma $N_2$ flush, 12 month aged coating | 2.2 | 2.24 | 2.56 | 2.3 | 0.014 |
| Prolene, Ethylene oxide sterilization | 2.78 | 2.16 | 1.94 | 2.29 | 0.019 |
| PPM3, No Sterilization, No Coating | 1.2 | 1.3 | 1 | 1.17 | |

Figure 6:
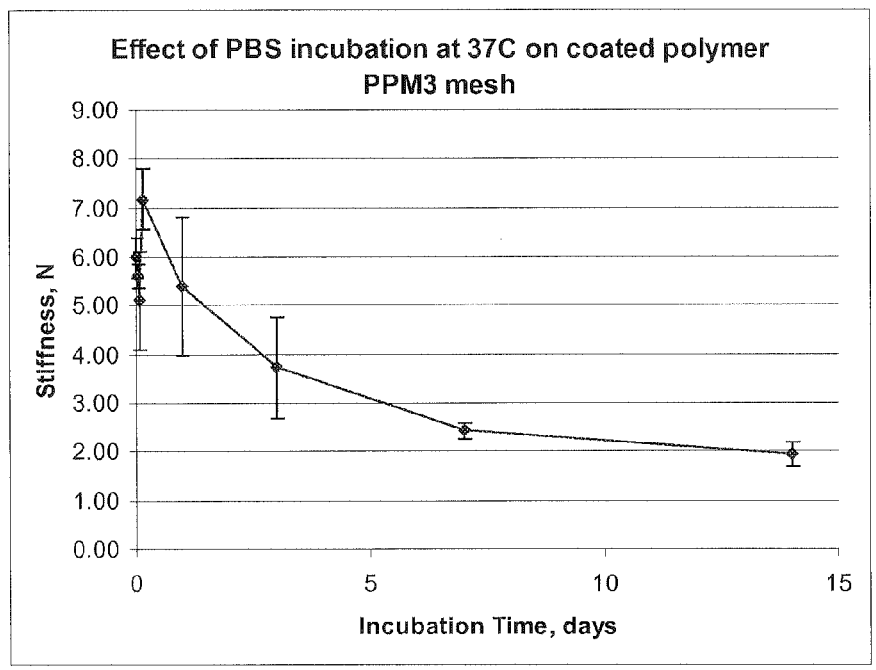
FIG. 6 graphically depicts the change in mesh stiffness over time during the course of polymer degradation for a polymer-coated polypropylene mesh soaking in PBS.

B. Meshes were prepared by spray coating a solution of P22-27.5 onto a PPM3 mesh as generally described in Example 1. the coated meshes were cut into 3" by 3" squares to provide 80 mg polymer coating per square. The squares were incubated in 1 L of 0.01 M PBS for the indicated times then removed for stiffness testing as described in part A of this Example. All experiments were done in triplicate. As a control, non-coated PPM3 meshes were incubated under the same conditions. The stiffness of the control when dry was 1.42±0.23 N when dry and 1.12 N after both 1 hour and 24 hour in 0.01 M PBS. The results are shown in FIG. 6.

Example 5

Micrographs of Coated Meshes

Figure 7:
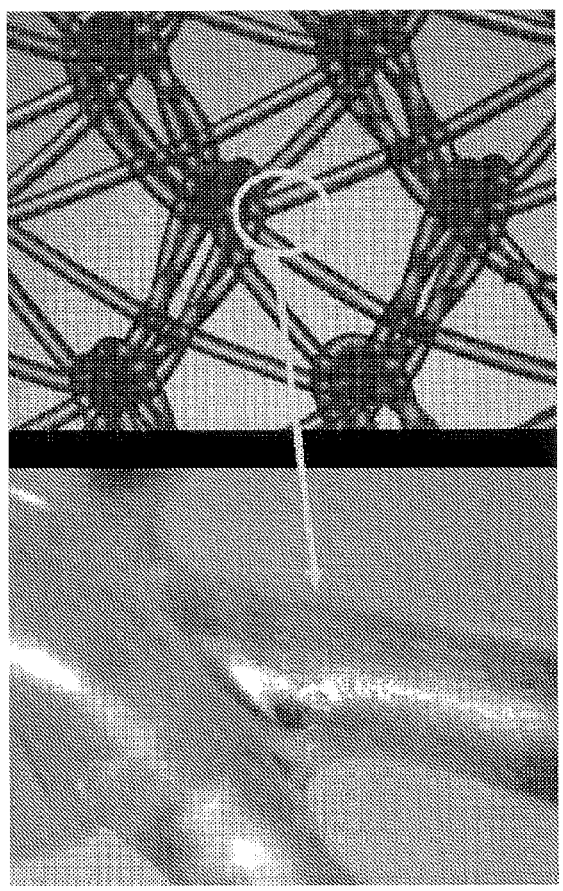
FIG. 7 depicts micrographs of a tyrosine polyarylate-coated mesh. The top left panel shows the woven nature of the mesh and the contact points of the filaments. The bottom left panel demonstrates the coating over the contact points of the mesh filaments. The right panel is a scanning electron micrograph of a coated filament.
Figure 7:
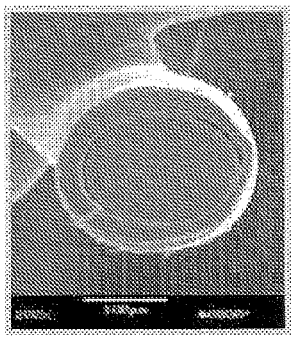

A tyrosine polyarylate-coated mesh without antibiotics, i.e., only a polymer coating, was prepared as described in Example 1 and omitting the antibiotics in the spray coating solution. An optical image of the coated mesh is shown in the top left panel of FIG. 7 at a magnification that readily shows the woven nature of the mesh and the contact points of the filaments. A close up of a contact point is shown in the bottom left panel of FIG. 7 and demonstrates that the coating immobilizes the contact points of the mesh filaments. The right panel of FIG. 7 is a scanning electron micrograph of a coated filament.

Figure 8:
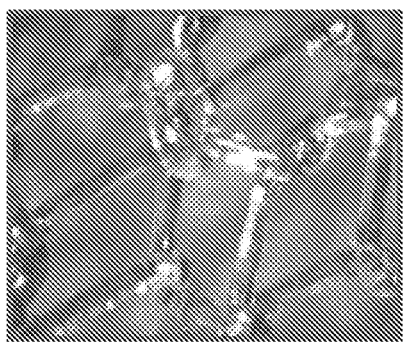
FIG. 8 provides an optical image of a mesh having a tyrosine polyarylate coating containing rifampin and minocycline. On the left, the optical image; on the right, a schematic thereof indicating the areas of intense orange color by the circled areas filled with diagonal lines.
Figure 8:
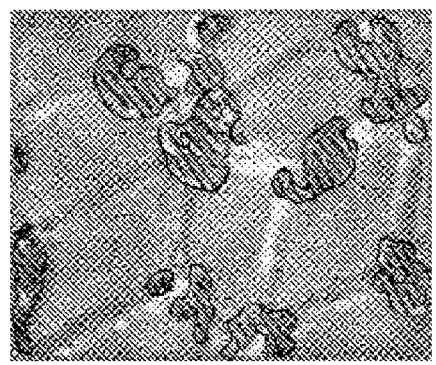

FIG. 8 shows an optical image of a mesh from Example 1, i.e., coated with polymer, rifampin and minocycline. In color, this photograph shows the mesh on a blue background with the filaments appearing greenish with some orange and the knots (or filament contact points) appearing mostly solid orange. The orange color is due to the antibiotics and is more visible on the knots due to the greater surface area of the mesh in that region. The color differentiation is difficult to visualize in the black and white version of this photograph so on the right panel the areas of orange are indicated by circled areas filled with diagonal lines.

REFERENCES

Hayes, B. B., Afshari, A., Millecchia, L., Willard, P. A., Povoski, S. P., Meade, B. J., 2000. Evaluation of percutaneous penetration of natural rubber latex proteins. Toxicol. Sci. 56, 262-270.

Khodorova, A. B., Strichartz, G. R., 2000. The addition of dilute epinephrine produces equieffectiveness of bupivacaine enantiomers for cutaneous analgesia in the rat. Anesth. Analg. 91, 410-416.

Kramer, C., Tawney, M., 1998. A fatal overdose of transdermally administered fentanyl. J. Am. Osteopath. Assoc. 98, 385-386.

Lau H, Patil N G, Lee F. Randomized clinical trial of postoperative subfascial infusion with bupivacaine following ambulatory open mesh repair of inguinal hernia. Dig Surg. 2003; 20(4):285-9.

LeBlanc K A, Bellanger D, Rhynes V K, Hausmann M Evaluation of a Continuous Infusion of 0.5% Marcaine via Elastomeric Pump for Postoperative Pain Management Following Open Inguinal Hernia Repair. J Am Coll Surg 2005; 200(2):198-202.

Morrow, T. J., Casey, K. L., 1983. Suppression of bulboreticular unit responses to noxious stimuli by analgesic mesencephalic stimulation. Somatosens. Res. 1, 151-168.

Sanchez B, Waxman K. Local anesthetic infusion pumps improve postoperative pain after inguinal hernia repair. The American Surgeon 2004; 70:1002-6.

We claim:

1. A surgical mesh prosthesis comprising a porous surgical woven or knitted mesh comprising a biocompatible material selected from the group consisting of polypropylene, polyesters and polyamides, said mesh formed into the configuration of a pouch for encapsulation of an implantable electronic device, whereby tissue ingrowth into said mesh stabilizes said implantable electronic device within said mesh, said surgical mesh coated with a biodegradable polymer coating, wherein said coating (i) temporarily imparts stiffness to said mesh to at least 1.1 times its uncoated stiffness, (ii) is disposed on said mesh without substantially altering the porosity thereof, (iii) biodegrades in the body of a patient to allow the mesh to revert substantially to its uncoated stiffness, (iv) has sufficient strength to hold said mesh in the form of said pouch once said coating is dried, cured or set, and (v) has a molecular weight of between 10,000 and 200,000 Dalton, said coating further comprising at least one drug miscible in said polymer coating selected from the group consisting of antimicrobial agents, anesthetics, analgesics, anti-fibrotic agents and leukotriene inhibitors.

2. The surgical mesh prosthesis of claim 1, wherein said coating is disposed on said mesh in a templated pattern.

3. The surgical mesh prosthesis of claim 1, wherein said biodegradable polymer is selected from the group consisting of a polylactic acid, polyglycolic acid, poly(L-lactide), poly (D,L-lactide), polyglycolic acid, poly(L-lactide-co-D,L-lactide), poly(L-lactide-co-glycolide), poly(D, L-lactide-co-glycolide), poly(glycolide-co-trimethylene carbonate), poly (D,L-lactide-co-caprolactone), poly(glycolide-co-caprolactone), polyoxaester, polydioxanone, polypropylene fumarate, poly(ethyl glutamate-co-glutamic acid), poly(tert-butyloxy-carbonylmethyl glutamate), polycaprolactone, polycaprolactone cobutylacrylate, polyhydroxybutyrate, poly(phosphazene), polyphosphate ester), poly(amino acid), polydepsipeptide, maleic anhydride copolymer, polyiminocarbonates, poly[(97.5% dimethyl-trimethylene carbonate)-co-(2.5% trimethylene carbonate)], poly(orthoesters), tyrosine-derived polyarylate, tyrosine-derived polycarbonate, tyrosine-derived polyiminocarbonate, tyrosine-derived polyphosphonate, protein, and blends of any thereof.

4. The surgical mesh prosthesis of claim 1, wherein said biodegradable polymer comprises a tyrosine-derived diphenol monomer unit.

5. The surgical mesh prosthesis of claim 4, wherein said biodegradable polymer is a polyarylate, polycarbonate, polyiminocarbonate or a polyphosphonate.

6. The surgical mesh prosthesis of claim 4, wherein said biodegradable polymer is a polyarylate.

7. The surgical mesh prosthesis of claim 6, wherein said polyarylate is a copolymer of desaminotyrosyl-tyrosine (DT) and desaminotyrosyl-tyrosine ethyl ester (DTE) succinate having from about 1% desaminotyrosyl-tyrosine (DT) to about 30% desaminotyrosyl-tyrosine (DT).

8. The surgical mesh prosthesis of claim 6, wherein said polyarylate is a random copolymer of desaminotyrosyl-tyrosine (DT) and an desaminotyrosyl-tyrosyl ester (DT ester), wherein said copolymer comprises from about 0.001% DT to about 80% DT and said ester moiety can be a branched or unbranched alkyl, alkylaryl, or alkylene ether group having up to 18 carbon atoms, any of group of which can, optionally have a polyalkylene oxide therein.

9. The surgical mesh prosthesis of claim 6, wherein said polyarylate is a random copolymer of 4-hydroxybenzoyl-tyrosine (BT) and 4-hydroxybenzoyl-tyrosyl ester (BT ester), wherein said copolymer comprises from about 0.001% BT to about 80% BT and said ester moiety can be a branched or unbranched alkyl, alkylaryl, or alkylene ether group having up to 18 carbon atoms, any of group of which can, optionally, have a polyalkylene oxide therein.

10. The surgical mesh prosthesis of claim 1, wherein said biodegradable polymer is a resorbable polymer.

11. The surgical mesh prosthesis of claim 1, wherein said mesh comprises polypropylene having a backing of expanded polytetrafluoroethylene (ePTFE).

12. The surgical mesh prosthesis of claim 1, wherein said mesh retains its original stiffness for about one week after implantation in a body of a patient.

13. The surgical mesh prosthesis of claim 1, wherein said drug is an antimicrobial agent.

14. The surgical mesh prosthesis of claim 13, wherein said antimicrobial agent is selected from the group consisting of rifampin, minocycline, silver/chlorhexidine, vancomycin, a cephalosporin, gentamycin, triclosan and combinations thereof.

15. The surgical mesh prosthesis of claim 1, wherein said at least one drug comprises rifampin in combination with another antimicrobial agent.

16. The surgical mesh prosthesis of claim 15, wherein said another antimicrobial agent is minocycline HCl.

17. The surgical mesh prosthesis of claim 1, wherein said porous mesh comprises pores of approximately 0.4 mm and approximately 3 mm.

18. The surgical mesh prosthesis of claim 1, wherein said mesh is non-resorbable.

19. The surgical mesh prosthesis of claim 1, wherein said coating is disposed on one or both sides of said mesh.

20. The surgical mesh prosthesis of claim 1, wherein said coating is disposed on substantially all of said mesh.

21. A coated surgical mesh prosthesis comprising:
    a knit or woven porous surgical mesh formed of polypropylene filaments defining pores in said porous mesh bounded by said filaments and knots formed by said filaments, said knit surgical mesh having a stiffness; and
    a coating disposed on said filaments and said knots of said surgical mesh, said coating
    (i) comprises a tyrosine-derived polyarylate;
    (ii) comprises an antimicrobial agent;
    (iii) imparts to said mesh an enhanced stiffness at least 1.1 times its uncoated stiffness; and
    (iv) biodegrades in a physiological solution to allow the mesh to revert substantially to its uncoated stiffness,
    said pores in said coated surgical mesh having a size of between approximately 0.4 mm and approximately 3 mm.

22. The surgical mesh prosthesis of claim 21, wherein said coating biodegrades to allow the mesh to revert substantially to its uncoated stiffness in about 3-4 months.

23. The surgical mesh prosthesis of claim 21, wherein said coating maintains an enhanced stiffness of at least 1.1 times the uncoated stiffness for at least about one week in a physiological solution.

24. The surgical mesh prosthesis of claim 21, wherein said antimicrobial agent is present in an amount effective to inhibit bacterial growth.

25. The surgical mesh prosthesis of claim 21, wherein said antimicrobial agent is present in an amount which provides a rate of drug release sufficient to prevent colonization of said mesh.

* * * * *